(12) United States Patent
Kim et al.

(10) Patent No.: US 11,401,275 B2
(45) Date of Patent: Aug. 2, 2022

(54) NON-FULLERENE BASED HETEROCYCLIC COMPOUND AND ORGANIC ELECTRONIC DEVICE INCLUDING SAME

(71) Applicant: LG CHEM, LTD., Seoul (KR)

(72) Inventors: Ji Hoon Kim, Daejeon (KR); Songrim Jang, Daejeon (KR); Doowhan Choi, Daejeon (KR); Jung Ha Park, Daejeon (KR); Bogyu Lim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 344 days.

(21) Appl. No.: 16/612,810

(22) PCT Filed: Apr. 2, 2019

(86) PCT No.: PCT/KR2019/003855
§ 371 (c)(1),
(2) Date: Nov. 12, 2019

(87) PCT Pub. No.: WO2019/221386
PCT Pub. Date: Nov. 21, 2019

(65) Prior Publication Data
US 2021/0323974 A1 Oct. 21, 2021

(30) Foreign Application Priority Data
May 17, 2018 (KR) .................. 10-2018-0056461

(51) Int. Cl.
*H01L 51/00* (2006.01)
*C07D 495/04* (2006.01)
(Continued)

(52) U.S. Cl.
CPC ........ *C07D 495/04* (2013.01); *H01L 51/0068* (2013.01); *C07D 409/00* (2013.01);
(Continued)

(58) Field of Classification Search
CPC . H01L 51/42; H01L 51/0032; H01L 51/0068; H01L 51/00; H01L 51/0036;
(Continued)

(56) References Cited

U.S. PATENT DOCUMENTS

2016/0181541 A1 6/2016 Lee et al.
2017/0309825 A1* 10/2017 Bazan ................. H01L 51/0036

FOREIGN PATENT DOCUMENTS

CN 107011361 8/2017
EP 2495272 9/2012
(Continued)

OTHER PUBLICATIONS

Li S. et al., An Unfused-Core-Based Nonfullerene Acceptor Enables High-Efficiency Organic Solar Cells with Excellent Morphological Stability at High Temperatures. Adv. Mater. 2018 (First publication date: Dec. 22, 2017), vol. 30, No. 6, article No. 1705208, inner pp. 1-8 (Year: 2017).*
(Continued)

*Primary Examiner* — Ermias T Woldegeorgis
(74) *Attorney, Agent, or Firm* — Myers Bigel, P.A.

(57) ABSTRACT

The present specification relates to a heterocyclic compound represented by Formula 1, an organic electronic device including the heterocyclic compound in an organic active layer, and a method for manufacturing the organic electronic device.

13 Claims, 2 Drawing Sheets

(51) Int. Cl.
*C07D 409/00* (2006.01)
*H01L 51/42* (2006.01)
*C07D 519/00* (2006.01)

(52) U.S. Cl.
CPC ........ *C07D 519/00* (2013.01); *H01L 51/0071* (2013.01); *H01L 51/4253* (2013.01)

(58) Field of Classification Search
CPC . H01L 51/0071; H01L 51/424; C07D 495/04; C07D 409/14; Y02E 10/549; Y02P 70/50
See application file for complete search history.

(56) References Cited

FOREIGN PATENT DOCUMENTS

| JP | 2012235076 | 11/2012 |
|---|---|---|
| KR | 1020120101400 | 9/2012 |
| KR | 101466716 | 12/2014 |
| KR | 1020160076926 | 7/2016 |
| WO | 2017/190345 | 11/2017 |

OTHER PUBLICATIONS

Cao et al. "Small-molecule acceptors based on 4H-cyclopenta[1,2-b:5,4-b']dithiophene units with near-infrared absorption for nonfullerene polymer solar cells" Synthetic Metals, 240:15-20 (2018).
Li et al. "An Unfused-Core-Based Nonfullerene Acceptor Enables High-Efficiency Organic Solar Cells with Excellent Morphological Stability at High Temperatures" Advanced Materials, 30(6):1705208 (2018) (8 pp).
Nowak-Krol et al. "Modulation of band gap and p- versus n-semiconductor character of ADA dyes by core and acceptor group variation" Organic Chemistry Frontiers, 3:545-555 (2016).
Tang, C.W. "Two-layer organic photovoltaic cell" Appl. Phys. Lett. 48(2) 183-185 (1986).
Yu et al. "Polymer Photovoltaic Cells: Enhanced Efficiencies via a Network of Internal Donor-Acceptor Heterojunctions" Science, 270(5243):1789-1791 (1995).

* cited by examiner

NON-FULLERENE BASED HETEROCYCLIC COMPOUND AND ORGANIC ELECTRONIC DEVICE INCLUDING SAME

CROSS REFERENCE TO RELATED APPLICATIONS

This application is a 35 U.S.C. § 371 national stage application of PCT International Application No. PCT/KR2019/003855, filed Apr. 2, 2019, which claims priority from Korean Patent Application No. 10-2018-0056461, filed May 17, 2018, the contents of which are incorporated herein in their entireties by reference.

TECHNICAL FIELD

The present specification relates to a heterocyclic compound and an organic electronic device including the same.

BACKGROUND ART

In the present specification, an organic electronic device is an electronic device using an organic semiconductor material, and requires exchanging of holes and/or electrons between electrodes and organic semiconductor materials. The organic electronic device may be roughly divided into the following two organic electronic devices depending on the operation principle. A first organic electronic device is an electronic device in which an exciton is formed in an organic material layer by a photon that flows from an external light source to the device, the exciton is separated into electrons and holes, and the electrons and the holes are each transferred to different electrodes and used as a current source (voltage source). A second organic electronic device is an electronic device in which holes and/or electrons are injected into organic semiconductor material layers forming an interface with an electrode by applying a voltage or current to two or more electrodes, and the device is operated by the injected electrons and holes.

Examples of the organic electronic device include an organic solar cell, an organic photoelectric device, an organic light emitting device, an organic photoconductor (OPC), an organic transistor, and the like, and an electron/hole injection material, an electron/hole extraction material, an electron/hole transport material or a light emitting material is required to drive all these devices. Hereinafter, an organic solar cell will be mainly described in detail, but in the organic electronic devices, all of an electron/hole injection material, an electron/hole extraction material, an electron/hole transport material, and a light emitting material are operated based on a similar principle.

A solar cell is a cell that changes electric energy directly from the sunlight, and studies have been actively conducted on the solar cell because the solar cell is a clean alternative energy source to solve the depletion of fossil energy and global environmental problems caused by the use thereof. Here, the solar cell means a cell which produces current-voltage by absorbing the photoenergy from the sunlight to use photovoltaic effects of generating electrons and holes.

The solar cell is a device which may directly convert solar energy into electric energy by applying a photovoltaic effect. The solar cell may be divided into an inorganic solar cell and an organic solar cell, depending on the materials constituting a thin film.

Numerous studies have been conducted on solar cells in order to increase the energy conversion efficiency through various layers and a change in electrode according to the design of the solar cell.

DETAILED DESCRIPTION OF INVENTION

Technical Problem

An object of the present invention is to provide a heterocyclic compound and an organic electronic device including the same.

Technical Solution

An exemplary embodiment of the present specification provides a heterocyclic compound represented by the following Formula 1.

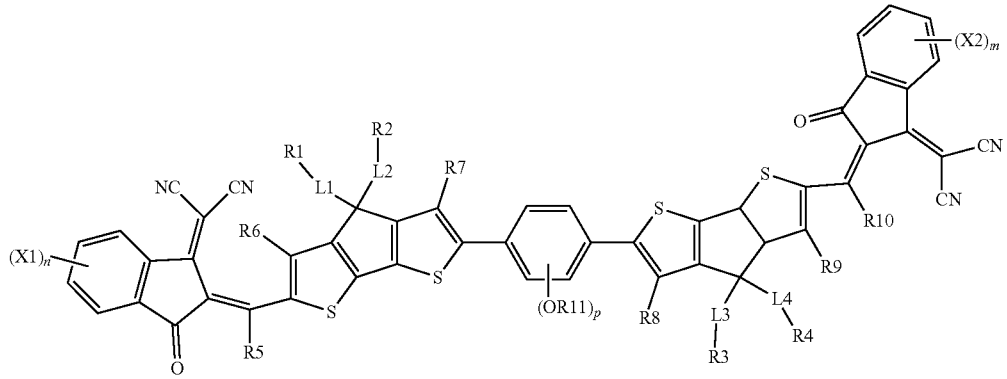

[Formula 1]

In Formula 1,

L1 to L4 are each a substituted or unsubstituted arylene group; or a substituted or unsubstituted divalent heterocyclic group, R1 to R11 are each hydrogen; or a substituted or unsubstituted alkyl group, X1 and X2 are each hydrogen; a substituted or unsubstituted alkyl group; or a halogen group, and m, n, and p are each an integer from 1 to 4.

Further, an exemplary embodiment of the present specification provides an organic electronic device including:

a first electrode;

a second electrode provided to face the first electrode; and an organic material layer having one or more layers provided between the first electrode and the second electrode and including an organic active layer, in which the organic active layer includes the heterocyclic compound.

In addition, an exemplary embodiment of the present specification provides a method for manufacturing an organic electronic device, the method including:

forming a first electrode on a substrate;

forming an electron transport layer on the first electrode;

forming an organic material layer having one or more layers and including an organic active layer on the electron transport layer; and forming a second electrode on the organic material layer, in which the organic active layer includes the heterocyclic compound.

Advantageous Effects

Since a heterocyclic compound according to an exemplary embodiment of the present specification has a wide light absorption region and a high LUMO energy level, a high level of efficiency may be obtained when the heterocyclic compound is used for an organic active layer of an organic electronic device.

EXPLANATION OF REFERENCE NUMERALS AND SYMBOLS

Figure 1:
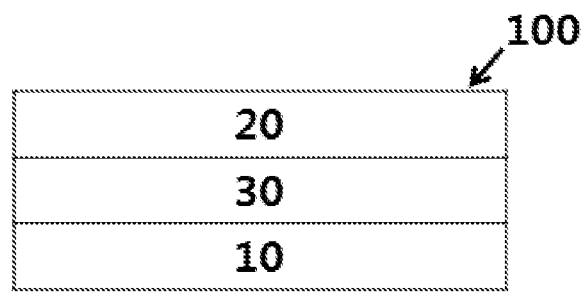
FIG. 1 is a view illustrating an organic solar cell according to an exemplary embodiment of the present specification.

10: First electrode
20: Second electrode
30: Photoactive layer
100: Organic solar cell

BEST MODE

Hereinafter, the present specification will be described in more detail.

An exemplary embodiment of the present specification provides the heterocyclic compound represented by Formula 1.

Studies on an organic electronic device in the related art have been focused on finding an electron donor material exhibiting high efficiency when an electron acceptor of an organic active layer is a fullerene compound such as PCBM, but since an organic electronic device including a fullerene compound has encountered a limitation in the performance such as an absorption region, an open-circuit voltage, and a service life of a device, studies on the utilization of a non-fullerene-based compound such as ITIC as an electron acceptor have been increasing.

The inventors of the present invention found out that by using, as an electron acceptor, the compound represented by Formula 1 in which the planarity is increased through interactions between O atoms and S atoms using dialkyloxyl-benzene as a core, even among non-fullerene-based compounds, it is possible to absorb light in a wider region than the electron acceptor material in the related art and to enhance the efficiency and stability of an organic electronic device including an organic solar cell.

When one part 'includes' one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

In the present specification, the energy level means a size of energy. Accordingly, even when the energy level is expressed in the negative (−) direction from the vacuum level, it is interpreted that the energy level means an absolute value of the corresponding energy value. For example, the HOMO energy level means the distance from the vacuum level to the highest occupied molecular orbital. Further, the LUMO energy level means the distance from the vacuum level to the lowest unoccupied molecular orbital.

In the present specification, the term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more substituents are substituted, the two or more substituents may be the same as or different from each other.

In the present specification, the term "substituted or unsubstituted" means being substituted with one or more substituents selected from the group consisting of deuterium; a halogen group; a hydroxyl group; an alkyl group; a cycloalkyl group; an alkoxy group; an aryloxy group; an alkenyl group; an aryl group; and a heterocyclic group, being substituted with a substituent to which two or more substituents among the exemplified substituents are linked, or having no substituent.

In the present specification, the number of carbon atoms of a substituent having a branched chain includes the number of carbon atoms of the branched chain. For example, '3 to 20' in 'an alkyl group having 3 to 20 carbon atoms and having one or more methyl groups as branched chains' is a numerical number including the number of carbon atoms of the 'one or more methyl groups'.

In the present specification, the alkyl group may be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

The alkyl group is substituted with an aryl group or a heteroaryl group, and thus may act as an arylalkyl group or a heteroarylalkyl group. The aryl group and the heteroaryl group may be selected from the examples of an aryl group and a heteroaryl group to be described below, respectively.

In the present specification, an aryl group may be monocyclic or polycyclic.

In the present specification, when the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

In the present specification, when the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto. The fluorenyl group may be substituted, and adjacent substituents may be bonded to each other to form a ring.

In the present specification, a heterocyclic group includes one or more atoms other than carbon, that is, one or more heteroatoms, and specifically, the heteroatom may include one or more atoms selected from the group consisting of O, N, Se, S, and the like. The number of carbon atoms of the heterocyclic group is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a phenothiazinyl group, a dibenzofuranyl group, and the like, but are not limited thereto.

The heterocyclic group may be monocyclic or polycyclic, and may be an aromatic ring, an aliphatic ring, or a condensed ring of the aromatic ring and the aliphatic ring.

In the present specification, the above-described description on the heterocyclic group may be applied to a heteroaryl group except for an aromatic heteroaryl group.

In the present specification, an arylene group means a group having two bonding positions in an aryl group, that is, a divalent group. The above-described description on the aryl group may be applied to the arylene group, except for a divalent arylene group.

In the present specification, a heteroarylene group means a group having two bonding positions in a heteroaryl group, that is, a divalent group. The above-described description on the heteroaryl group may be applied to the heteroarylene group, except for a divalent heteroarylene group.

An exemplary embodiment of the present specification provides the compound represented by Formula 1.

In an exemplary embodiment of the present specification, p is 2, and OR11's in the parenthesis may be the same as or different from each other and may be substituted with each other at the para position of a benzene ring.

In an exemplary embodiment of the present specification, n and m are each 1 or 2.

In an exemplary embodiment of the present specification, n and m are each 1.

In an exemplary embodiment of the present specification, n and m are each 2.

In an exemplary embodiment of the present specification, X1 and X2 are each hydrogen or fluorine.

In an exemplary embodiment of the present specification, X1 and X2 are each hydrogen.

In an exemplary embodiment of the present specification, X1 and X2 are each fluorine.

In an exemplary embodiment of the present specification, X1 and X2 are each a straight-chained alkyl group having 1 to 10 carbon atoms.

In an exemplary embodiment of the present specification, X1 and X2 are each a methyl group.

In an exemplary embodiment of the present specification, Formula 1 may be represented by the following Formula 1-1.

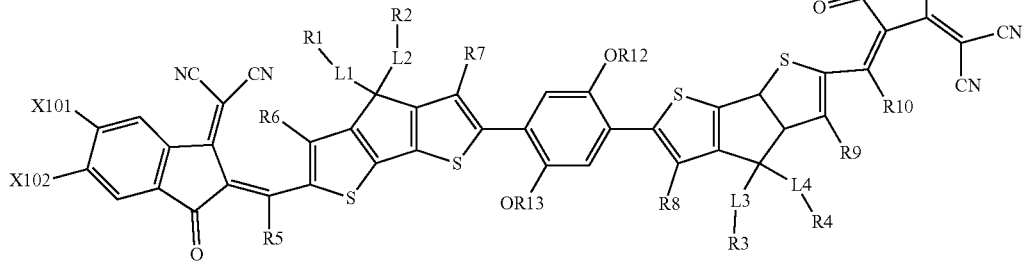

[Formula 1-1]

In Formula 1-1,

R1 to R10 and L1 to L4 are the same as those defined in Formula 1,

R12 and R13 are each hydrogen; or a substituted or unsubstituted alkyl group, and X101, X102, X201, and X202 are each hydrogen; a substituted or unsubstituted alkyl group; or a halogen group.

In an exemplary embodiment of the present specification, L1 to L4 are each a phenylene group or a divalent thiophene group.

In an exemplary embodiment of the present specification, Formula 1 may be represented by the following Formula 1-2 or 1-3.

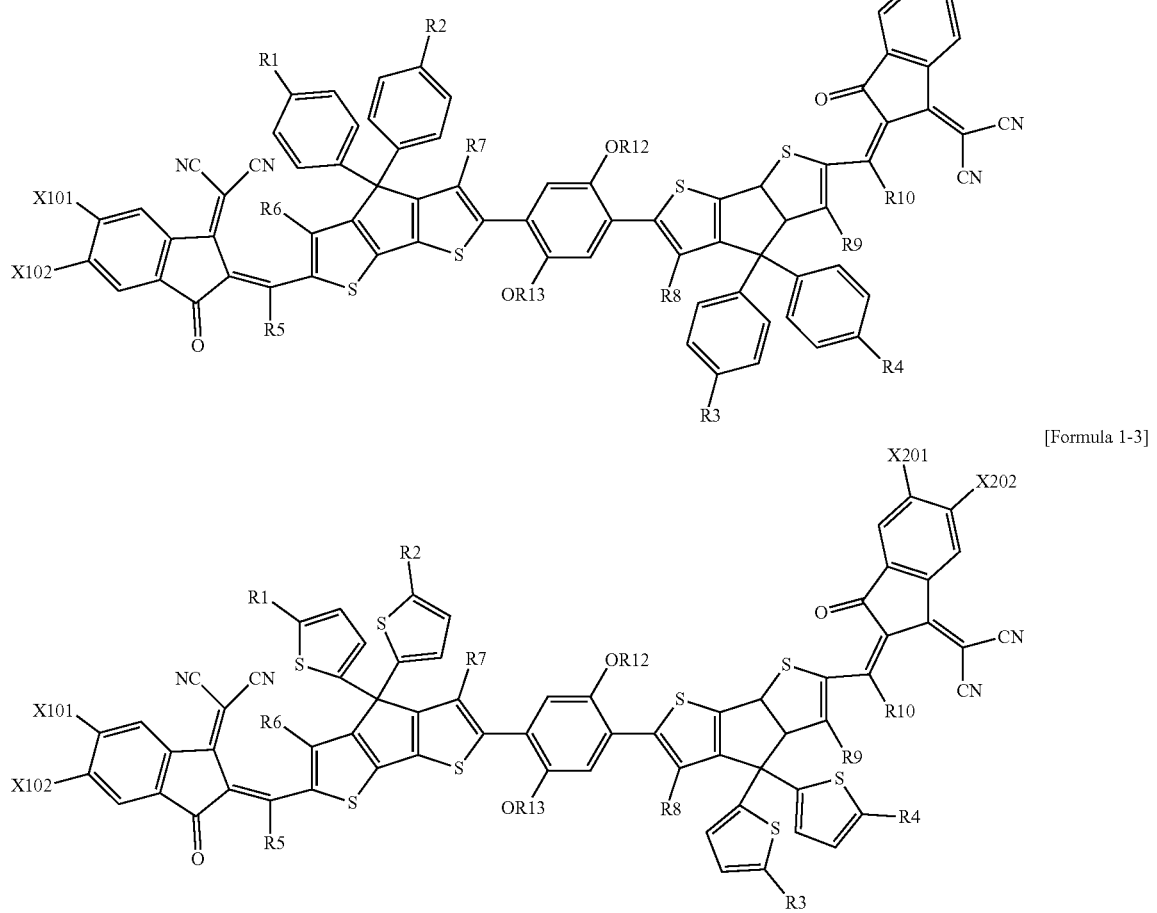

In Formulae 1-2 and 1-3,

R1 to R10 are the same as those defined in Formula 1,

R12 and R13 are each hydrogen; or a substituted or unsubstituted alkyl group, and X101, X102, X201, and X202 are each hydrogen; a substituted or unsubstituted alkyl group; or a halogen group.

In an exemplary embodiment of the present specification, X101, X102, X201, and X202 are each hydrogen.

In an exemplary embodiment of the present specification, X101, X102, X201, and X202 are each fluorine.

In an exemplary embodiment of the present specification, X101, X102, X201, and X202 are each a straight-chained alkyl group having 1 to 10 carbon atoms.

In an exemplary embodiment of the present specification, X101, X102, X201, and X202 are each a methyl group.

In an exemplary embodiment of the present specification, R1 to R4 are each a substituted or unsubstituted alkyl group.

In an exemplary embodiment of the present specification, R1 to R4 are each a straight-chained or branched alkyl group having 1 to 30 carbon atoms.

In an exemplary embodiment of the present specification, R1 to R4 are each a straight-chained or branched alkyl group having 1 to 20 carbon atoms.

In an exemplary embodiment of the present specification, R1 to R4 are each a straight-chained or branched alkyl group having 1 to 10 carbon atoms.

In an exemplary embodiment of the present specification, R1 to R4 are each a straight-chained alkyl group having 1 to 10 carbon atoms.

In an exemplary embodiment of the present specification, R1 to R4 are each a hexyl group.

In an exemplary embodiment of the present specification, R5 to R10 are each hydrogen.

In an exemplary embodiment of the present specification, R11 is a straight-chained or branched alkyl group having 1 to 30 carbon atoms.

In an exemplary embodiment of the present specification, R11 is a straight-chained or branched alkyl group having 1 to 20 carbon atoms.

In an exemplary embodiment of the present specification, R11 is a straight-chained or branched alkyl group having 1 to 10 carbon atoms.

In an exemplary embodiment of the present specification, R11 is a straight-chained alkyl group having 1 to 10 carbon atoms.

In an exemplary embodiment of the present specification, R11 is a hexyl group.

In an exemplary embodiment of the present specification, R12 and R13 are each a straight-chained or branched alkyl group having 1 to 30 carbon atoms.

In an exemplary embodiment of the present specification, R12 and R13 are each a straight-chained or branched alkyl group having 1 to 20 carbon atoms.

In an exemplary embodiment of the present specification, R12 and R13 are each a straight-chained or branched alkyl group having 1 to 10 carbon atoms.

In an exemplary embodiment of the present specification, R12 and R13 are each a straight-chained alkyl group having 1 to 10 carbon atoms.

In an exemplary embodiment of the present specification, R12 and R13 are each a hexyl group.

In an exemplary embodiment of the present specification, the heterocyclic compound is represented by any one of the following Formulae 2-1 to 2-15.

[Formula 2-1]

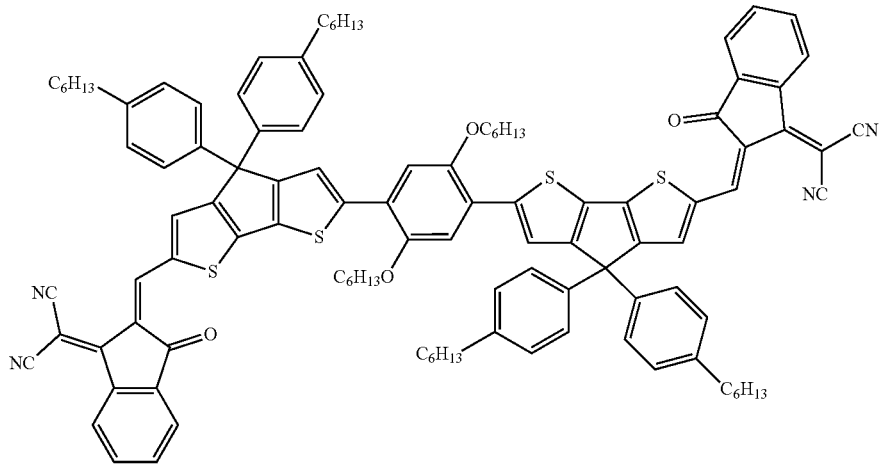

[Formula 2-2]

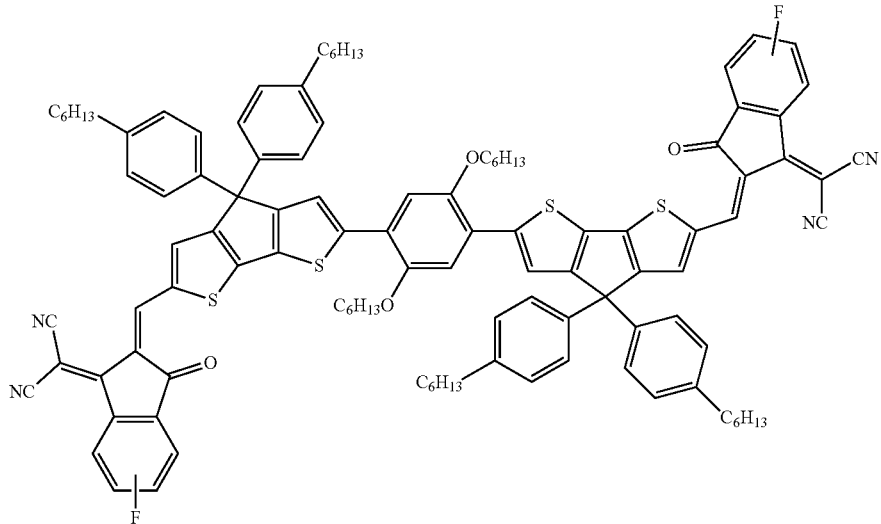

[Formula 2-3]
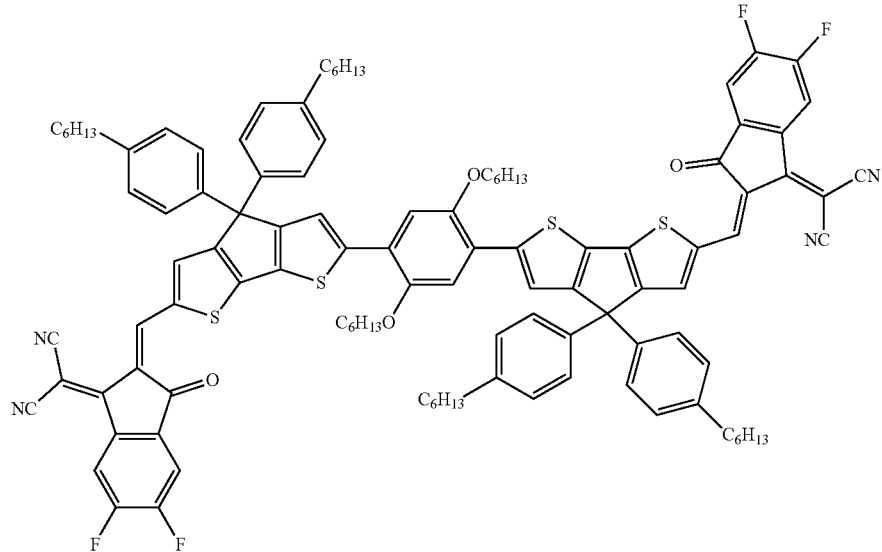
[Formula 2-4]
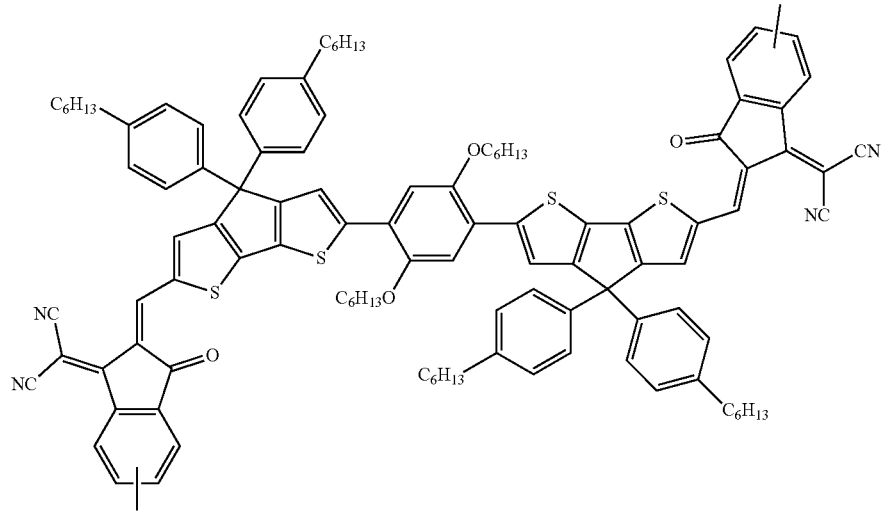
[Formula 2-5]
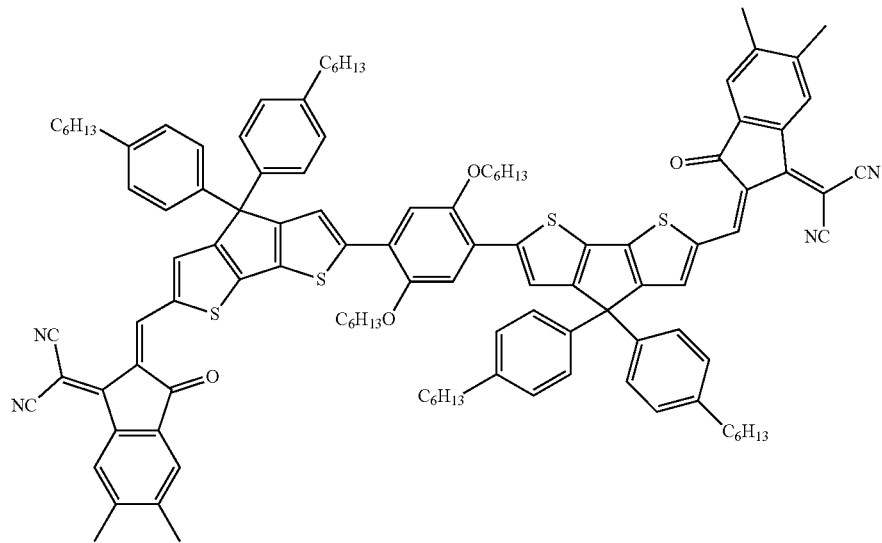

[Formula 2-6]
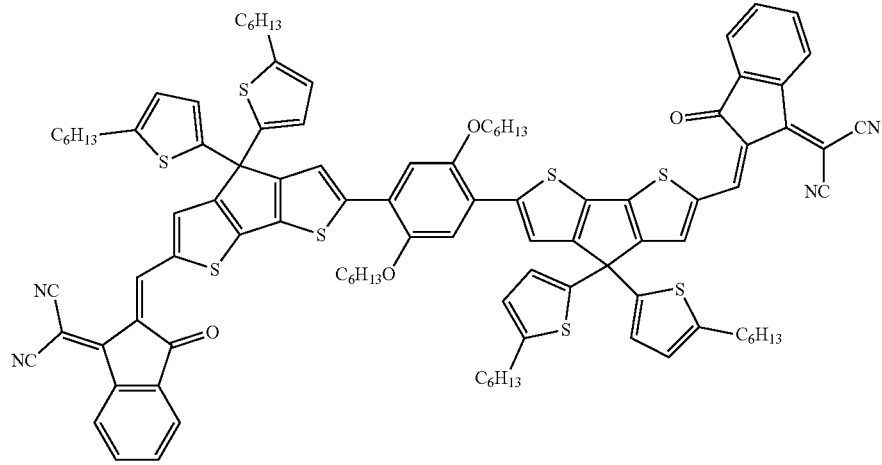
[Formula 2-7]
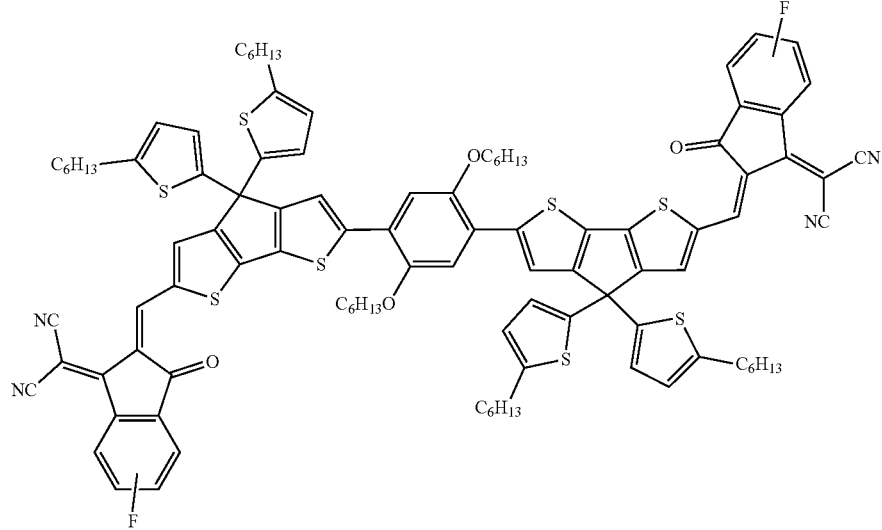
[Formula 2-8]
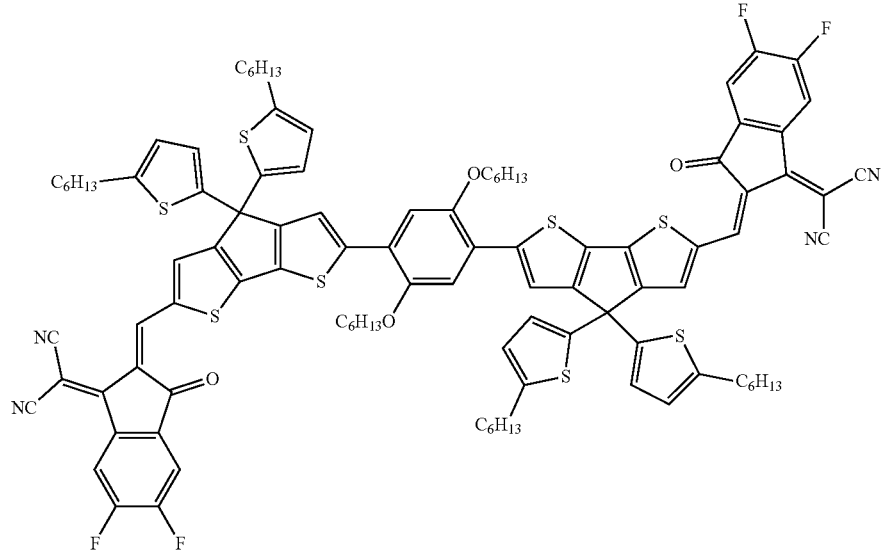

[Formula 2-9]
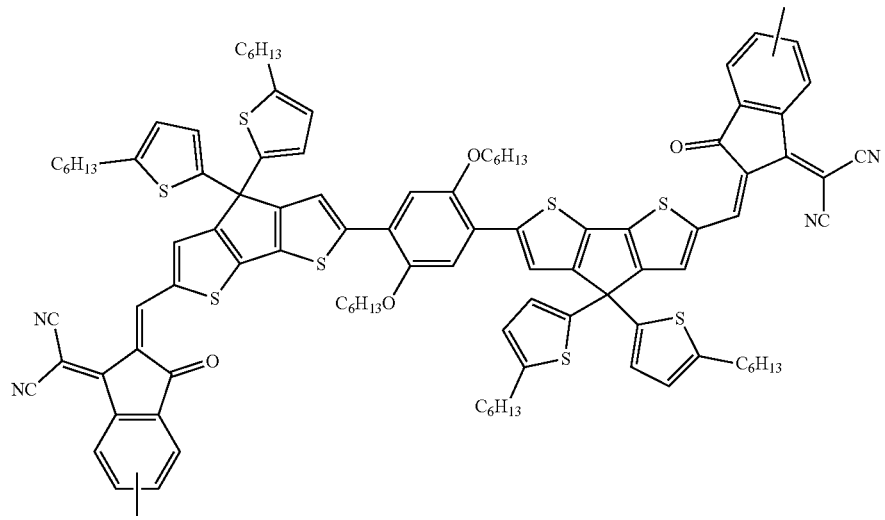
[Formula 2-10]
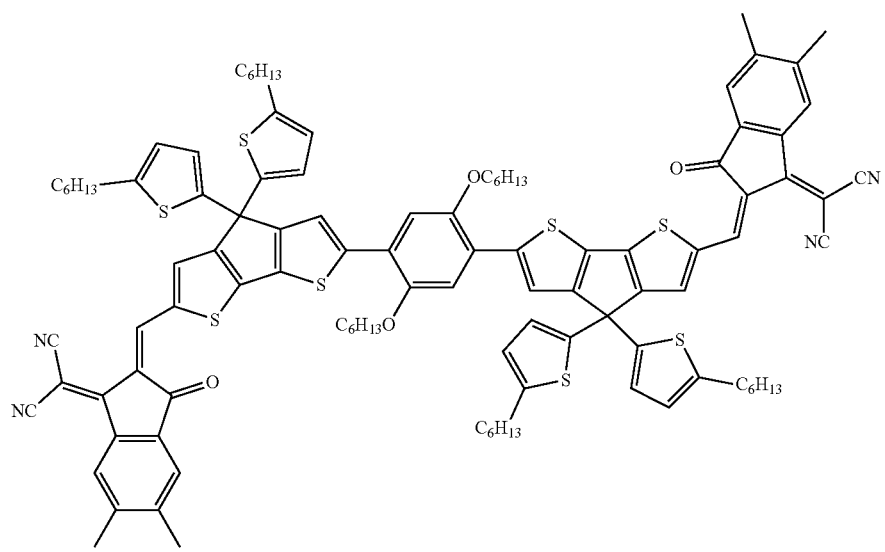
[Formula 2-11]
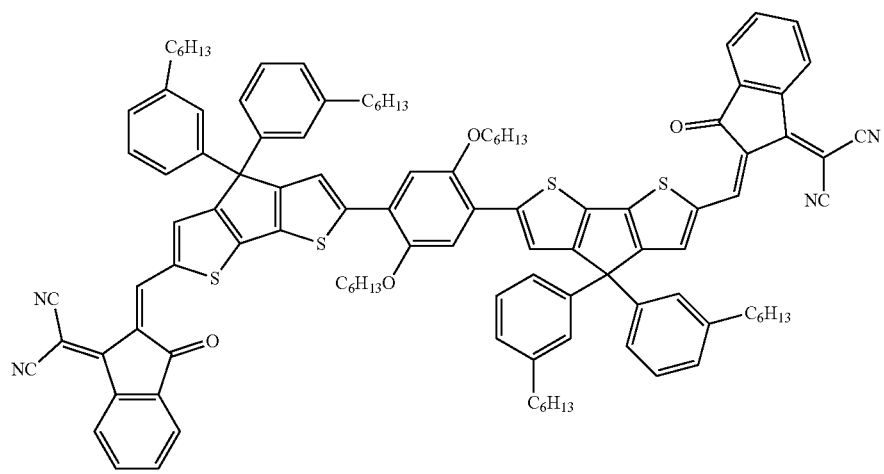

[Formula 2-12]
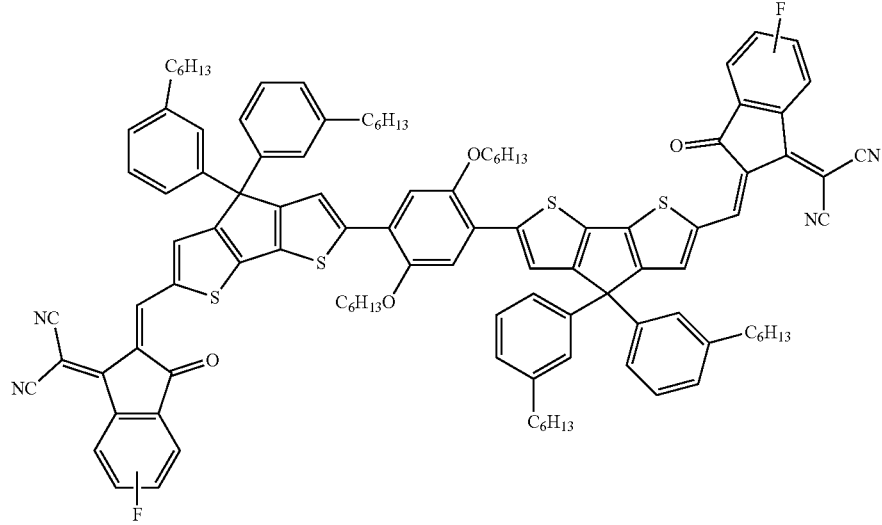
[Formula 2-13]
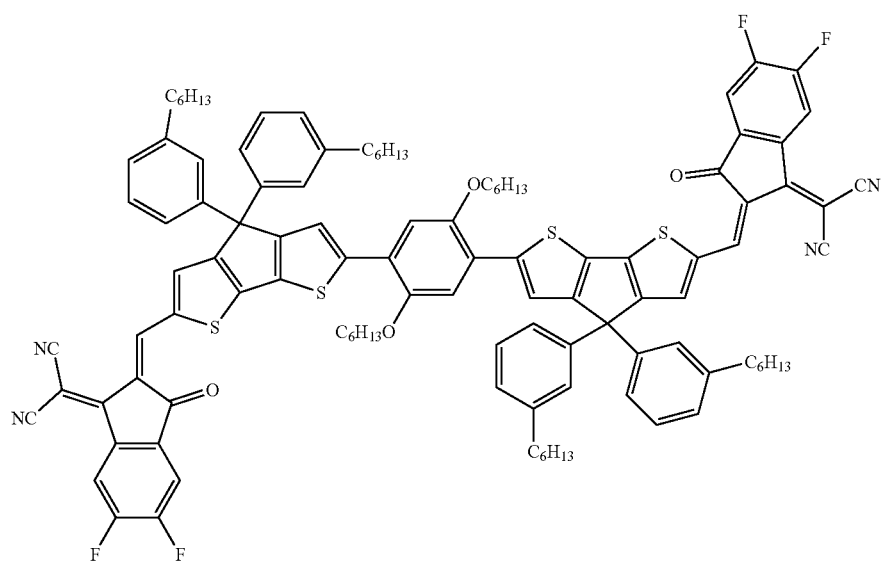
[Formula 2-14]
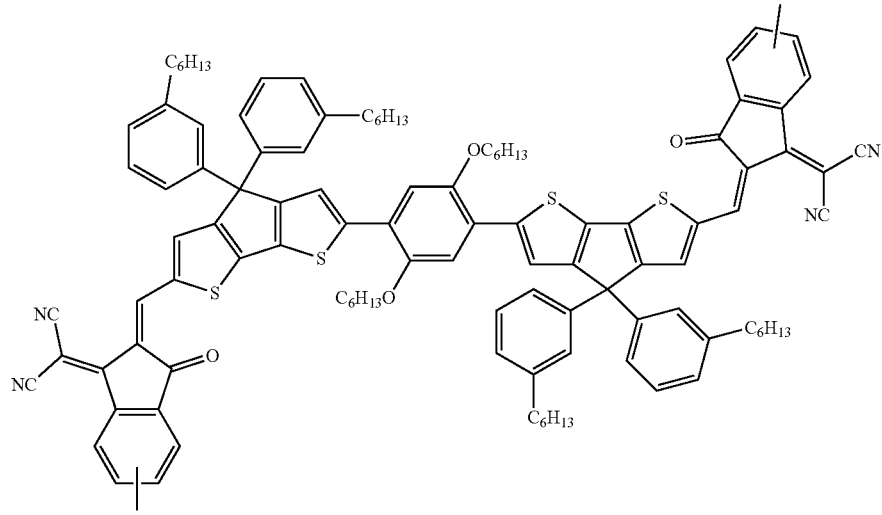

[Formula 2-15]

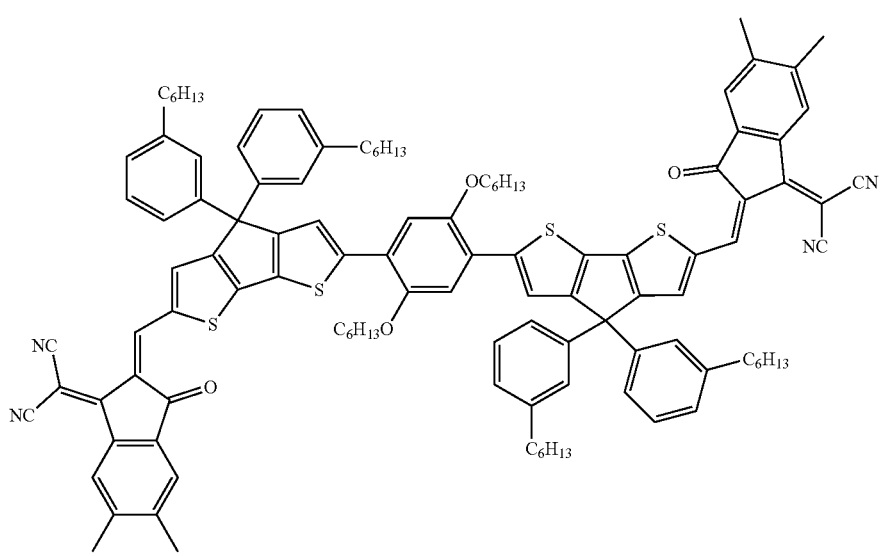

In Formulae 2-1 to 2-15, the case where a structure represented as

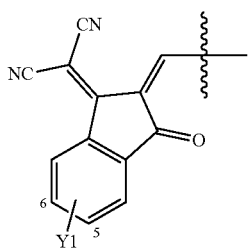

is included means that a compound in which Y1 is substituted at the No. 5 position and a compound in which Y1 is substituted at the No. 6 position are mixed, and a mass ratio of the compound in which Y1 is substituted at the No. 5 position to the compound in which Y1 is substituted at the No. 6 position may be 1:9 to 9:1, and specifically 7:3.

In an exemplary embodiment of the present specification, the heterocyclic compound exhibits an absorption region from 300 nm to 1,000 nm, and preferably has a maximum absorption wavelength at 700 nm to 900 nm.

Accordingly, when the heterocyclic compound is applied to an organic electronic device, a complementary absorption with an absorption region (300 nm to 700 nm) of an electron donor is exhibited, so that a high short-circuit current may be exhibited when the heterocyclic compound is applied to the organic electronic device.

In an exemplary embodiment of the present specification, the compound can absorb light in the entire visible light wavelength region, and can also absorb light in the infrared ray region. Accordingly, the compound may exhibit an effect in which the absorption wavelength range of the device is broad.

An exemplary embodiment of the present specification provides an organic electronic device including: a first electrode; a second electrode provided to face the first electrode; and an organic material layer having one or more layers provided between the first electrode and the second electrode and including an organic active layer, in which the organic active layer includes the heterocyclic compound.

Further, an exemplary embodiment of the present specification provides a method for manufacturing an organic electronic device, the method including: forming a first electrode on a substrate; forming an electron transport layer on the first electrode; forming an organic material layer having one or more layers and including an organic active layer on the electron transport layer; and forming a second electrode on the organic material layer, in which the organic active layer includes the heterocyclic compound.

In an exemplary embodiment of the present specification, the forming of the organic material layer having one or more layers and including the organic active layer may be performed by a spin-coating method, and the spin-coating rate may be 1,300 rpm to 1,600 rpm.

When the spin-coating rate is within the above range, the thickness of the organic active layer may be formed within 100 nm, so that the performance of the organic electronic device may be improved.

The organic electronic device of the present invention may be manufactured by typical methods and materials for manufacturing an organic electronic device, except that the heterocyclic compound represented by Formula 1 is included in an organic active layer.

In an exemplary embodiment of the present specification, the organic active layer includes an electron donor and an electron acceptor, and the electron acceptor includes the heterocyclic compound.

In the present specification, the organic active layer may be a photoactive layer or a light emitting layer.

In the present specification, the organic electronic device may be an organic solar cell, an organic photoelectric device, an organic light emitting device, an organic photoconductor (OPC), or an organic transistor.

Hereinafter, an organic solar cell will be exemplified. In the organic solar cell, an organic active layer is a photoactive layer, and the above-described organic electronic device may cite the description on an organic solar cell described below.

An exemplary embodiment of the present specification provides an organic solar cell including: a first electrode; a second electrode provided to face the first electrode; and an organic material layer having one or more layers provided between the first electrode and the second electrode and including a photoactive layer, in which the photoactive layer includes the heterocyclic compound.

The organic solar cell may further include a substrate, a hole transport layer, a hole injection layer, an electron injection layer, and/or an electron transport layer.

In an exemplary embodiment of the present specification, the organic solar cell may further include an additional organic material layer. The organic solar cell may reduce the number of organic material layers by using an organic material which simultaneously has various functions.

In an exemplary embodiment of the present specification, the photoactive layer includes an electron donor and an electron acceptor, and the electron acceptor includes the heterocyclic compound.

An electron acceptor material including the heterocyclic compound may exhibit an improved performance as compared to an electron acceptor material in the related art by applying dialkyloxyl-benzene as a core to the electron acceptor material. Specifically, when the heterocyclic compound is used as an electron acceptor material of an organic solar cell, it is possible to absorb light in a wider region than the electron acceptor material in the related art because the planarity is increased due to the interactions between O atoms and S atoms. Accordingly, a high short-circuit current density may be obtained, an improved open-circuit voltage due to the change in LUMO energy level may be obtained, and ultimately, the photo-electric conversion efficiency of an organic solar cell may be enhanced.

In an exemplary embodiment of the present specification, a material applied in the art may be used as the electron donor, and for example, the electron donor may include one or more materials selected from the group consisting of poly 3-hexyl thiophene (P3HT), poly[N-9'-heptadecanyl-2,7-carbazole-alt-5,5-(4'-7'-di-2-thienyl-2',1',3'-benzothiadiazole)] (PCDTBT), poly[2,6-(4,4-bis-(2-ethylhexyl)-4H-cyclopenta [2,1-b;3,4-b']dithiophene)-alt-4,7-(2,1,3-benzothiadiazole)] (PCPDTBT), poly[2,7-(9,9-dioctylfluorene)-alt-5,5-(4,7-bis (thiophene-2-yl)benzo-2,1,3-thiadiazole)](PFO-DBT), poly [[4,8-bis[(2-ethylhexyl)oxy]benzo[1,2-b:4,5-b']dithi-ophene-2,6-diyl][3-fluoro-2-[(2-ethylhexyl)carbonyl]thieno [3,4-b]thiophenediyl]] (PTB7), poly[2,7-(9,9-dioctyl-dibenzosilole)-alt-4,7-bis(thiophen-2-yl)benzo-2,1,3-thiadiazole] (PSiF-DBT), poly[4,8-bis(5-(2-ethylhexyl) thiophen-2-yl)benzo[1,2-b;4,5-b']dithiophene-2,6-diyl-alt-(4-(2-ethylhexyl)-3-fluorothieno[3,4-b]thiophene-)-2-carboxylate-2-6-diyl)](PTB7-Th), and poly (benzodithiophene-benzotriazole) (PBDB-T).

In an exemplary embodiment of the present specification, the electron donor may be PBDB-T.

A mass ratio of the electron donor to the electron acceptor may be 1:2 to 2:1, preferably 1:1.5 to 1.5:1, and more preferably 1:1.

In an exemplary embodiment of the present specification, the electron donor and the electron acceptor may constitute a bulk heterojunction (BHJ). The bulk heterojunction means that an electron donor material and an electron acceptor material are mixed with each other in a photoactive layer.

In an exemplary embodiment of the present specification, the electron donor may be a p-type organic material layer, and the electron acceptor may be an n-type organic material layer.

In an exemplary embodiment of the present specification, the first electrode is an anode, and the second electrode is a cathode. In another exemplary embodiment, the first electrode is a cathode, and the second electrode is an anode.

In still another exemplary embodiment, in the organic solar cell, an anode, a hole transport layer, a photoactive layer, an electron transport layer, and a cathode may also be arranged in this order, and a cathode, an electron transport layer, a photoactive layer, a hole transport layer, and an anode may also be arranged in this order, but the arrangement order is not limited thereto.

In an exemplary embodiment of the present specification, the organic solar cell has a normal structure. In the normal structure, a substrate, a first electrode, a hole transport layer, an organic material layer including a photoactive layer, an electron transport layer, and a second electrode may be stacked in this order.

In an exemplary embodiment of the present specification, the organic solar cell has an inverted structure. In the inverted structure, a substrate, a first electrode, an electron transport layer, an organic material layer including a photoactive layer, a hole transport layer, and a second electrode may be stacked in this order.

FIG. 1 is a view illustrating an organic solar cell 100 according to an exemplary embodiment of the present specification. According to FIG. 1, in the organic solar cell 100, light is incident from the sides of a first electrode 10 and/or a second electrode 20, so that when a photoactive layer 30 absorbs light in the entire wavelength region, excitons may be formed inside thereof. The exciton is separated into a hole and an electron in the photoactive layer 30, the separated hole moves to an anode side which is one of the first electrode 10 and the second electrode 20, and the separated electron moves to a cathode side which is the other of the first electrode 10 and the second electrode 20, so that an electric current may flow in the organic solar cell.

In an exemplary embodiment of the present specification, the organic solar cell has a tandem structure. In this case, the organic solar cell may include a photoactive layer having two or more layers.

The organic solar cell according to an exemplary embodiment of the present specification may have a photoactive layer having one or two or more layers.

In another exemplary embodiment, a buffer layer may be provided between a photoactive layer and a hole transport layer, or between a photoactive layer and an electron transport layer. In this case, a hole injection layer may be further provided between an anode and the hole transport layer. Further, an electron injection layer may be further provided between a cathode and the electron transport layer.

In the present specification, the substrate may be a glass substrate or a transparent plastic substrate having excellent transparency, surface smoothness, ease of handling, and water proof properties, but is not limited thereto, and is not limited as long as the substrate is a substrate typically used in an organic solar cell. Specific examples thereof include glass, polyethylene terephthalate (PET), polyethylene naphthalate (PEN), polypropylene (PP), polyimide (PI), triacetyl cellulose (TAC), and the like, but are not limited thereto.

A material for the first electrode may be a material which is transparent and has excellent conductivity, but is not limited thereto. Examples thereof include: a metal, such as vanadium, chromium, copper, zinc, and gold, or an alloy thereof; a metal oxide, such as zinc oxide, indium oxide, indium tin oxide (ITO), and indium zinc oxide (IZO); a combination of metal and oxide, such as $ZnO:Al$ or $SnO_2$:Sb; a conductive polymer, such as poly(3-methylthiophene), poly[3,4-(ethylene-1,2-dioxy)thiophene](PEDOT), polypyrrole, and polyaniline; and the like, but are not limited thereto.

A method of forming the first electrode is not particularly limited, but it is possible to use a method such as sputtering, e-beam, thermal deposition, spin coating, screen printing, inkjet printing, doctor blade, or gravure printing.

When the first electrode is formed on a substrate, the first electrode may be subjected to processes of cleaning, removing moisture, and hydrophilic modification.

For example, a patterned ITO substrate is sequentially cleaned with a cleaning agent, acetone, and isopropyl alcohol (IPA), and then dried on a hot plate at 100° C. to 150° C. for 1 to 30 minutes, preferably at 120° C. for 10 minutes in order to remove moisture, and when the substrate is completely cleaned, the surface of the substrate is hydrophilically modified.

Through the surface modification described above, the junction surface potential may be maintained at a level suitable for a surface potential of a photoactive layer. Further, during the modification, a polymer thin film may be easily formed on the first electrode, and the quality of the thin film may also be improved.

Examples of a pre-treatment technology for a first electrode include a) a surface oxidation method using a parallel flat plate-type discharge, b) a method of oxidizing the surface through ozone produced by using UV rays in a vacuum state, c) an oxidation method using oxygen radicals produced by plasma, and the like.

One of the methods may be selected according to the state of the first electrode or the substrate. However, although any method is used, it is preferred to commonly prevent oxygen from being separated from the surface of the first electrode or the substrate, and maximally inhibit moisture and organic materials from remaining. In this case, it is possible to maximize a substantial effect of the pre-treatment.

As a specific example, it is possible to use a method of oxidizing the surface through ozone produced by using UV. In this case, a patterned ITO substrate after being ultrasonically cleaned is baked on a hot plate and dried well, and then introduced into a chamber, and the patterned ITO substrate may be cleaned by ozone generated by allowing an oxygen gas to react with UV light by operating a UV lamp.

However, the surface modification method of the patterned ITO substrate in the present specification need not be particularly limited, and any method may be used as long as the method is a method of oxidizing a substrate.

The second electrode may be a metal having a low work function, but is not limited thereto. Specific examples thereof include: a metal such as magnesium, calcium, sodium, potassium, titanium, indium, yttrium, lithium, gadolinium, aluminum, silver, tin, and lead, or an alloy thereof; and a multi-layer structured material such as LiF/Al, LiO$_2$/Al, LiF/Fe, Al:Li, Al:BaF$_2$, and Al:BaF$_2$:Ba, but are not limited thereto.

The second electrode may be deposited and formed in a thermal evaporator showing a vacuum degree of 5×10$^{-7}$ torr or less, but the forming method is not limited to this method.

A material for the hole transport layer and/or a material for the electron transport layer serve/serves to efficiently transfer electrons and holes separated from a photoactive layer to an electrode, and the materials are not particularly limited.

The material for the hole transport layer may be poly(3,4-ethylenedioxythiophene) doped with poly(styrenesulfonic acid) (PEDOT:PSS); molybdenum oxide (MoO$_x$); vanadium oxide (V$_2$O$_5$); nickel oxide (NiO); tungsten oxide (WO$_x$); and the like, but is not limited thereto.

The material for the electron transport layer may be bathocuproine (BCP) or electron-extracting metal oxides, and specific examples thereof include: bathocuproine (BCP); metal complexes of 8-hydroxyquinoline; complexes including Alq$_3$; metal complexes including Liq; LiF; Ca; titanium oxide (TiO$_x$); zinc oxide (ZnO); and cesium carbonate (Cs$_2$CO$_3$); and the like, but are not limited thereto.

In an exemplary embodiment of the present specification, as a method for forming the photoactive layer, a vacuum deposition method or a solution application method may be used, the solution application method means a method of dissolving a photoactive material such as an electron donor and/or an electron acceptor in an organic solvent, and then applying the solution by using a method such as spin coating, dip coating, screen printing, spray coating, doctor blade, or brush painting, but the method is not limited to these methods.

The compound according to an exemplary embodiment of the present specification may be prepared by a preparation method described below. Representative examples will be described in the Preparation Examples described below, but if necessary, a substituent may be added or excluded, and the position of the substituent may be changed. Further, a starting material, a reactant, reaction conditions, and the like may be changed based on the technology known in the art.

Hereinafter, the present specification will be described in detail with reference to Examples in order to specifically explain the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

Mode for Invention

PREPARATION EXAMPLES: PREPARATION OF COMPOUNDS 1 TO 15>

Preparation Example 1. Preparation of Compound 1

(1) Preparation of Compound A

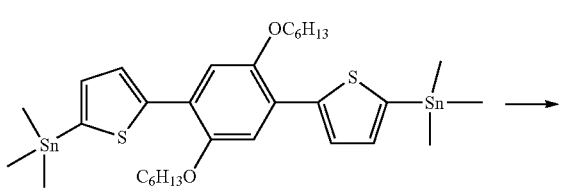

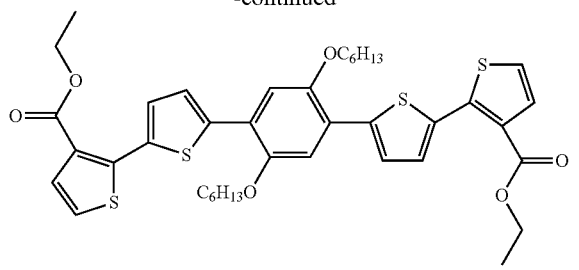

Compound A

After 5 g of ((2,5-bis(hexyloxy)-1,4-phenylene)bis(thiophene-5,2-diyl))bis(trimethylstannane)), 0.43 g of $Pd_2(dba)_3$, and 0.57 g of tri(o-tolyl)phosphine) were dissolved in 150 mL of toluene in a round flask equipped with a condenser, the resulting solution was refluxed. When the temperature became 100° C. 1-5.15 g (2.5 eq) of ethyl 2-bromothiophene-3-carboxylate was dissolved in 5 mL of toluene, and the resulting solution was slowly injected thereinto, and then refluxed for 12 hours. After the reaction was terminated, Compound A (diethyl 5',5'''-(2,5-bis(hexyloxy)-1,4-phenylene)bis([2,2'-bithiophene]-3-carboxylate)) was obtained through column chromatography.

(2) Preparation of Compound B

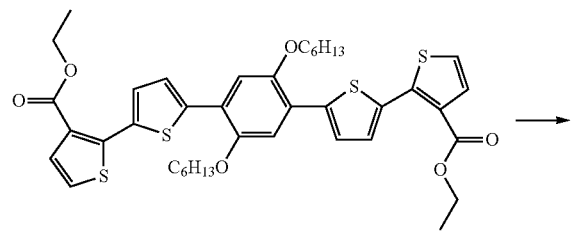

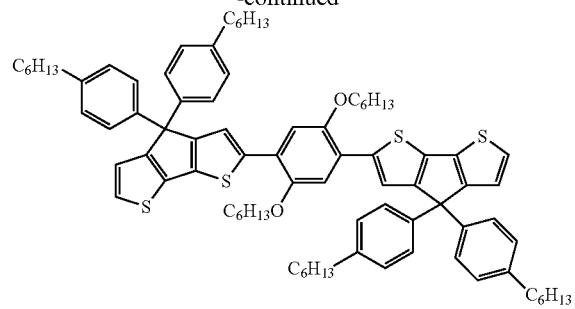

Compound B

After 8.16 g (5.3 eq) of 1-bromo-4-hexylbenzene was dissolved in 200 mL of THF in a round flask, 13.5 mL of n-BuLi was slowly injected to the resulting solution at −78° C., and then the resulting mixture was stirred at the same temperature for 1 hour. After Compound A prepared in (1) was dissolved in 50 mL of THF, the resulting solution was slowly injected into the round flask under stirring, and then stirred at room temperature for 12 hours. After the organic layer was extracted through chloroform, the solvent was removed, the residue was dissolved in 100 mL of octane, 10 mL of acetic acid, and 1 mL of sulfuric acid, and then the resulting solution was refluxed at 65° C. for 4 hours. The reaction was terminated through distilled water and Compound B (2,2'-(2,5-bis(hexyloxy)-1,4-phenylene)bis(4,4-bis(4-hexylphenyl)-4H-cyclopenta[2,1-b:3,4-b']dithiophene)) was obtained through column chromatography.

(3) Preparation of Compound C

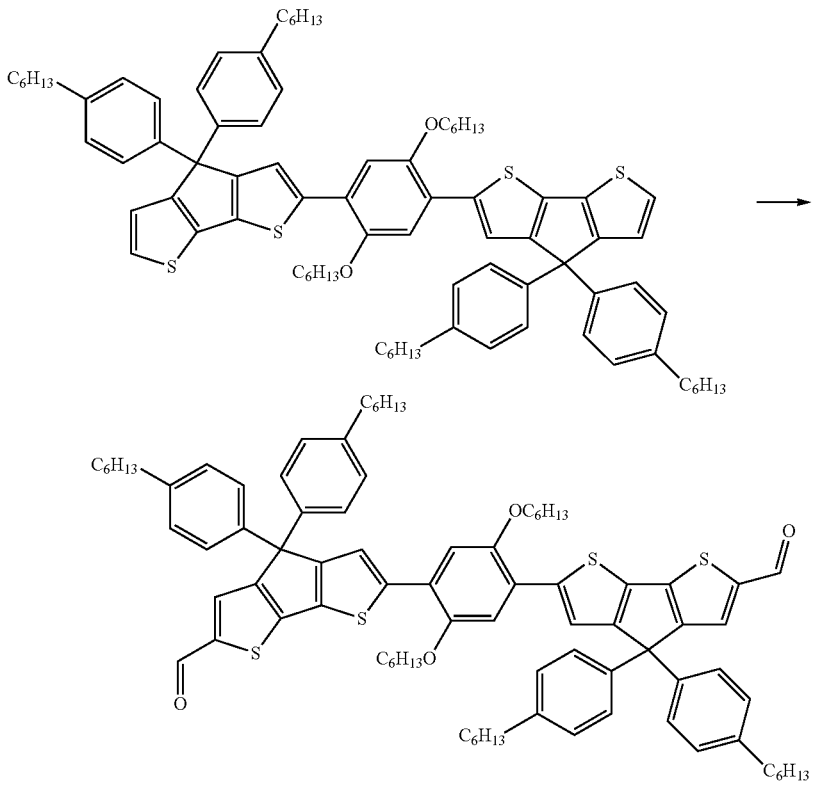

Compound C 1 g of Compound B prepared in (2) was dissolved in 100 mL of THF in a round flask, and then 0.76 mL of n-BuLi was slowly injected to the resulting solution at −78° C. After the mixture was stirred at the same temperature for 1 hour, 0.5 mL of DMF was slowly injected thereinto, and the resulting mixture was stirred for 12 hours. After the reaction was terminated through distilled water, the organic layer was extracted, and then Compound C (6,6'-(2,5-bis(hexyloxy)-1,4-phenylene)bis(4,4-bis(4-hexylphenyl)-4H-cyclopenta[2,1-b:3,4-b']dithiophene-2-carbaldehyde)) was obtained through column chromatography.

(4) Preparation of Compound 1

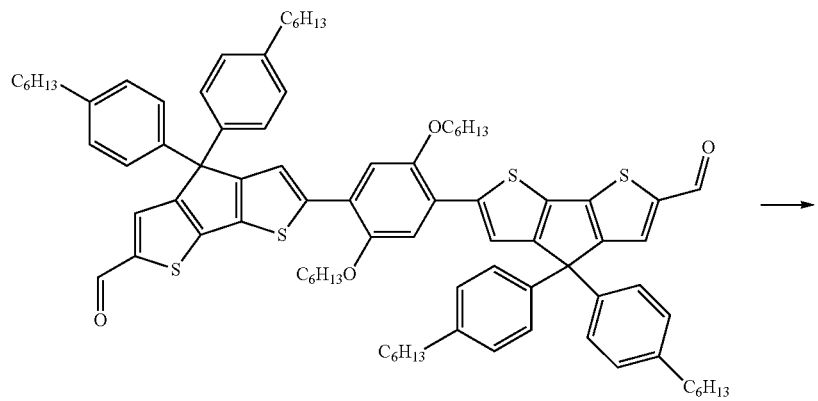

1 g of Compound C prepared in (3) and 0.7 g of 2-(3-oxo-2,3-dihydro-1H-inden-1-ylidene)malononitrile were dissolved in 10 mL of chloroform in a round flask equipped with a condenser, 1 mL of pyridine was injected to the resulting solution, and the resulting mixture was refluxed at 60° C. for 12 hours. After filtration through methanol, Compound 1 (2,2'-((2Z,2'Z)-(((2,5-bis(hexyloxy)-1,4-phenylene)bis(4,4-bis(4-hexylphenyl)-4H-cyclopenta[2,1-b:3,4-b']dithiophene-6,2-diyl))bis(methanylylidene))bis(3-oxo-2,3-dihydro-1H-indene-2,1-diylidene))dimalononitrile) was obtained through column chromatography.

Figure 2:
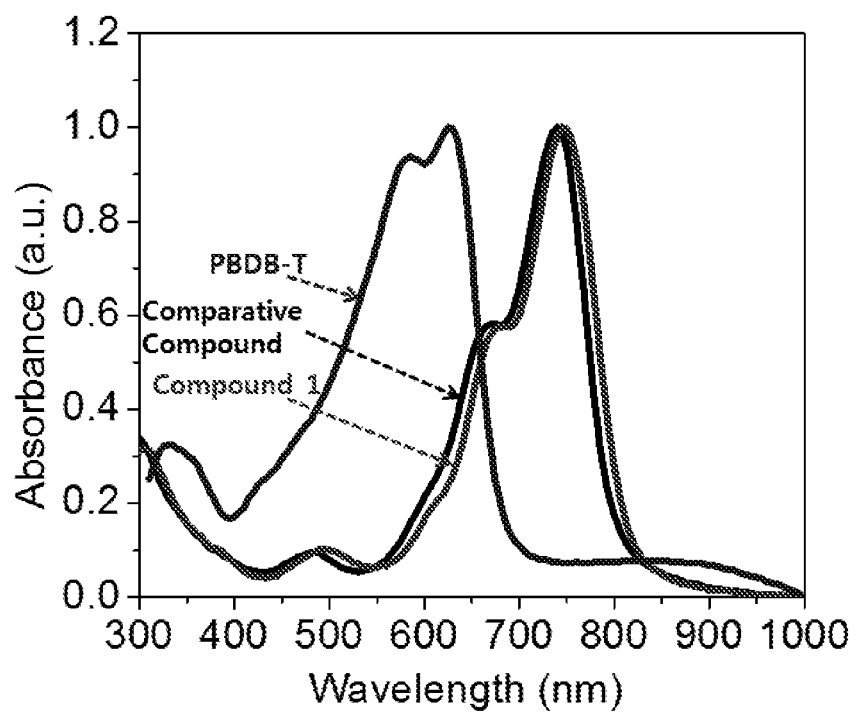
FIG. 2 is a graph illustrating UV-Vis absorption spectra of Compound 1, PBDB-T, and a Comparative Compound in a film state.

The UV spectrum of prepared Compound 1 in a film state is illustrated in FIG. 2.

Preparation Example 2. Preparation of Compounds 2 to 5

The following Compounds 2 to 5 were prepared by performing the same process as in Preparation Example 1,

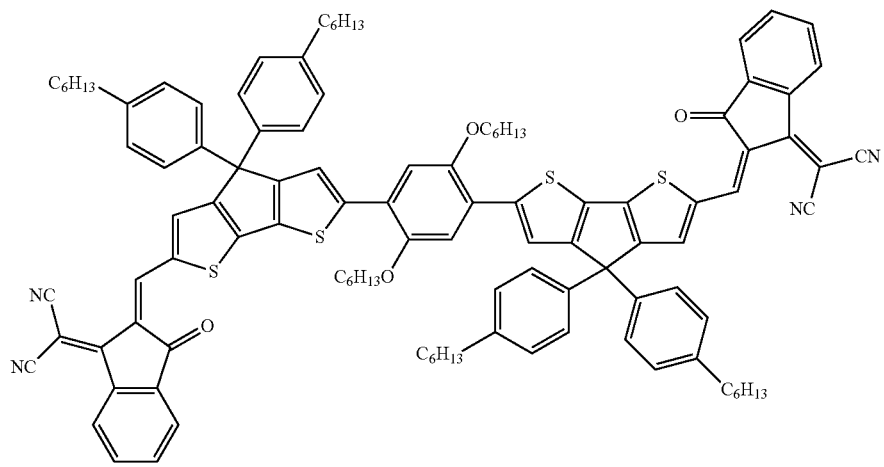

Compound 1 except that the respective materials in the following Table 1 were used instead of 2-(3-oxo-2,3-dihydro-1H-inden-1-ylidene)malononitrile in (4) of Preparation Example 1.

TABLE 1

| Target compound | Used material |
| --- | --- |
| Compound 2 | Compound in which 2-(6-fluoro-3-oxo-2,3-dihydro-1H-inden-1-ylidene)malononitrile and 2-(5-fluoro-3-oxo-2,3-dihydro-1H-inden-1-ylidene)malononitrile are mixed at a mass ratio of 3:7 |
| Compound 3 | (2-(5,6-difluoro-3-oxo-2,3-dihydro-1H-inden-1-ylidene)malononitrile) |
| Compound 4 | Compound in which 2-(6-methyl-3-oxo-2,3-dihydro-1H-inden-1-ylidene)malononitrile and 2-(5-methyl-3-oxo-2,3-dihydro-1H-inden-1-ylidene)malononitrile are mixed at a mass ratio of 3:7 |
| Compound 5 | 2-(5,6-dimethyl-3-oxo-2,3-dihydro-1H-inden-1-ylidene)malononitrile |

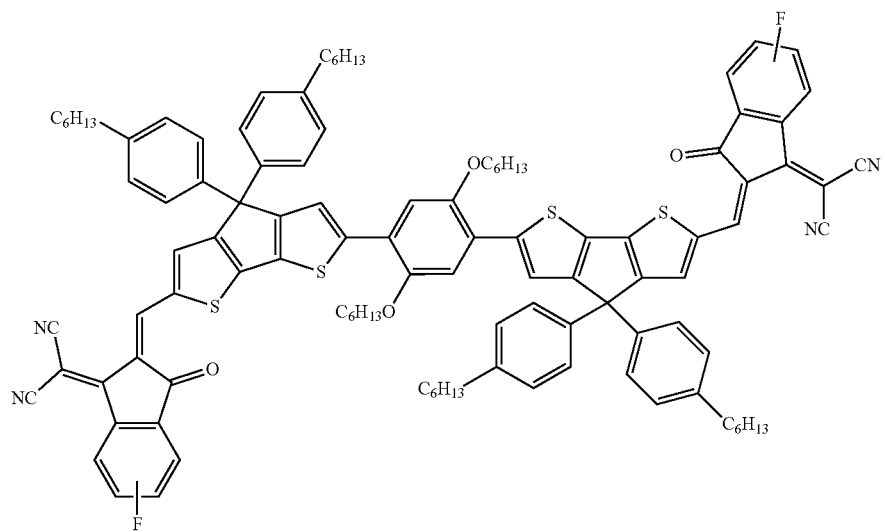

[Compound 2]

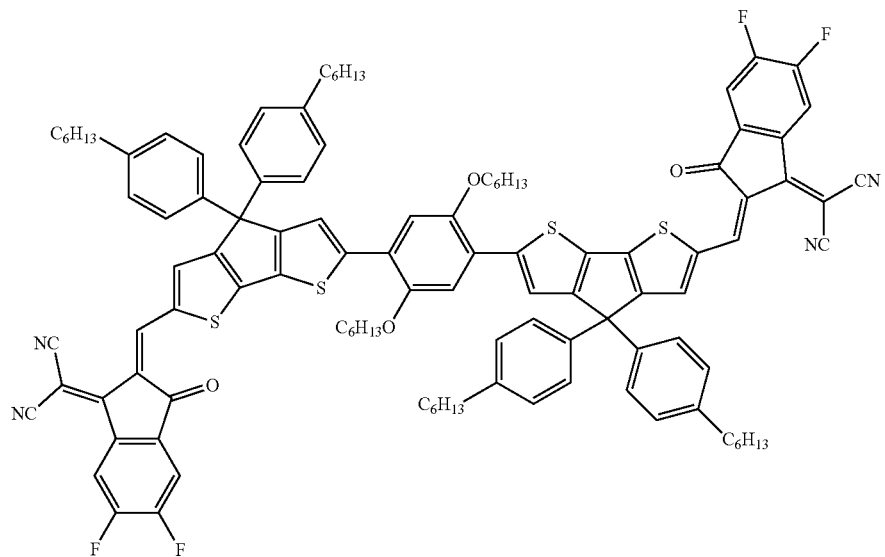

[Compound 3]

[Compound 4]
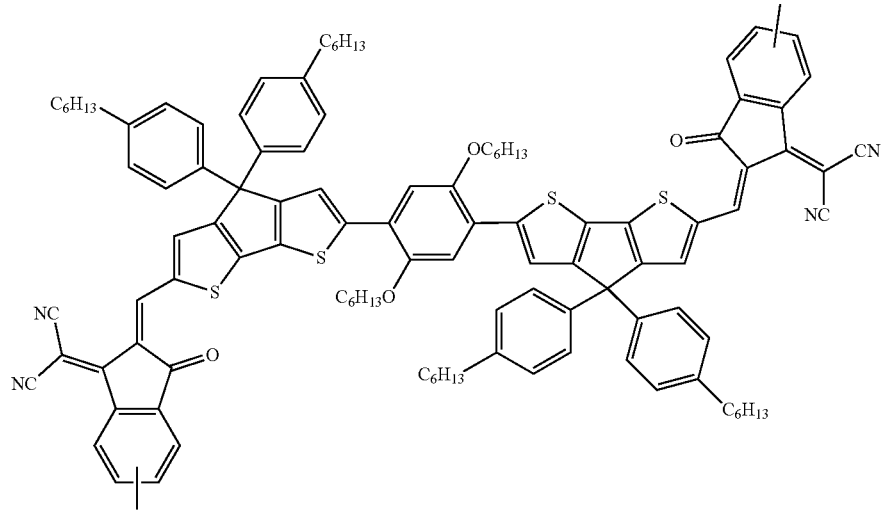
[Compound 5]
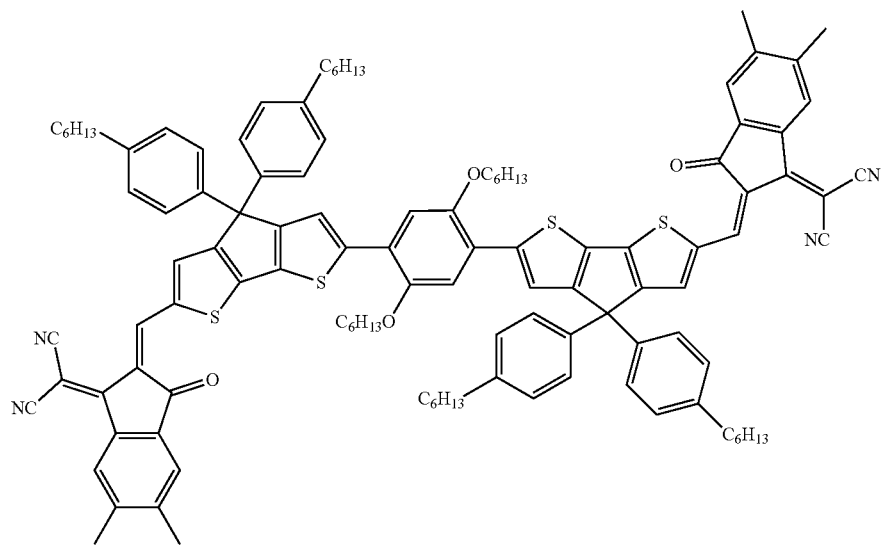
Preparation Example 3. Preparation of Compound 6
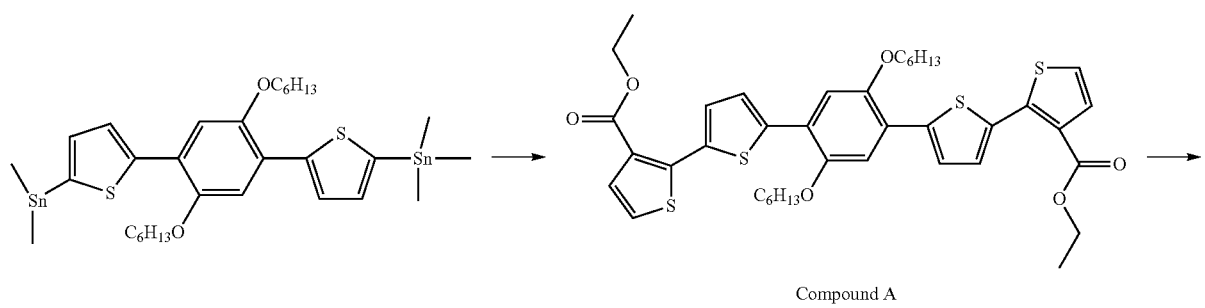
Compound A -continued

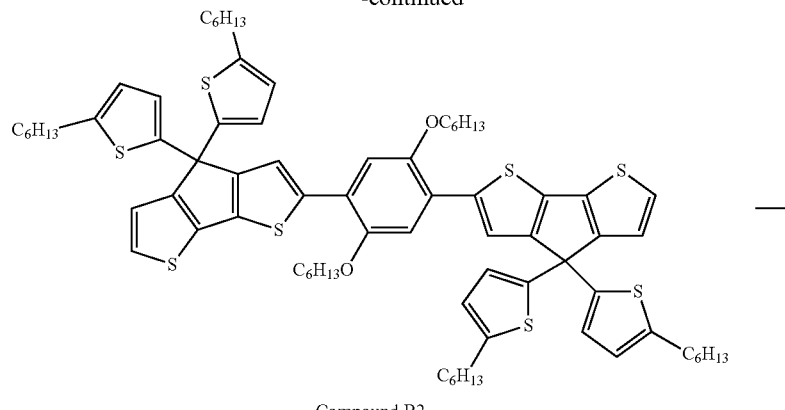
Compound B2

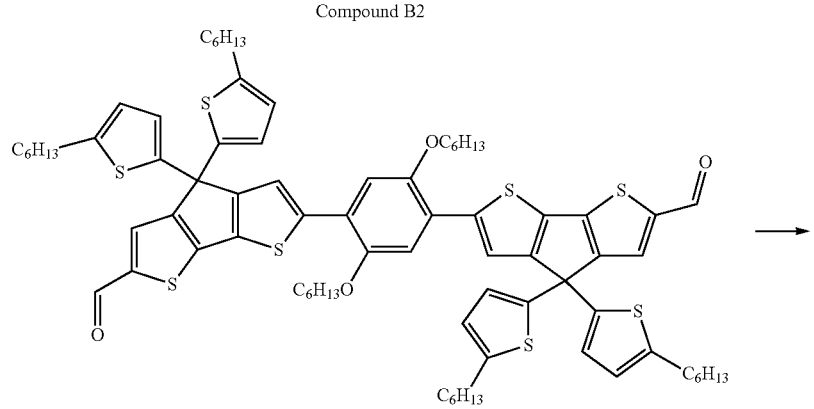
Compound C2

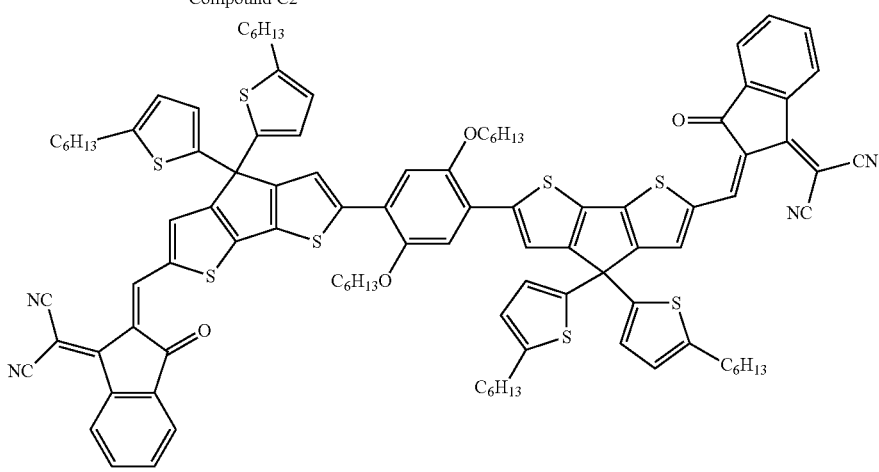
Compound 6

(1) Preparation of Compound B2

Compound B2 was prepared by performing the same process as in (2) of Preparation Example 1, except that 2-hexylthiophene was used instead of 1-bromo-4-hexylbenzene in (2) of Preparation Example 1.

(2) Preparation of Compound C2

Compound C2 was prepared by performing the same process as in (3) of Preparation Example 1, except that Compound B2 was used instead of Compound B in (3) of Preparation Example 1.

(3) Production of Compound 6

Compound 6 was prepared by performing the same process as in (4) of Preparation Example 1, except that Compound C2 was used instead of Compound C in (4) of Preparation Example 1.

Preparation Example 4. Preparation of Compounds 7 to 10

The following Compounds 7 to 10 were prepared by performing the same process as in Preparation Example 3, except that the respective materials in the following Table 2 were used instead of 2-(3-oxo-2,3-dihydro-1H-inden-1-ylidene)malononitrile in (3) of Preparation Example 3.

TABLE 2

| Target compound | Used material |
|---|---|
| Compound 7 | Compound in which 2-(6-fluoro-3-oxo-2,3-dihydro-1H-inden-1-ylidene)malononitrile and 2-(5-fluoro-3-oxo-2,3-dihydro-1H-inden-1-ylidene)malononitrile are mixed at a mass ratio of 3:7 |
| Compound 8 | (2-(5,6-difluoro-3-oxo-2,3-dihydro-1H-inden-1-ylidene)malononitrile) |
| Compound 9 | Compound in which 2-(6-methyl-3-oxo-2,3-dihydro-1H-inden-1-ylidene)malononitrile and 2-(5-methyl-3-oxo-2,3-dihydro-1H-inden-1-ylidene)malononitrile are mixed at a mass ratio of 3:7 |
| Compound 10 | 2-(5,6-dimethyl-3-oxo-2,3-dihydro-1H-inden-1-ylidene)malononitrile |

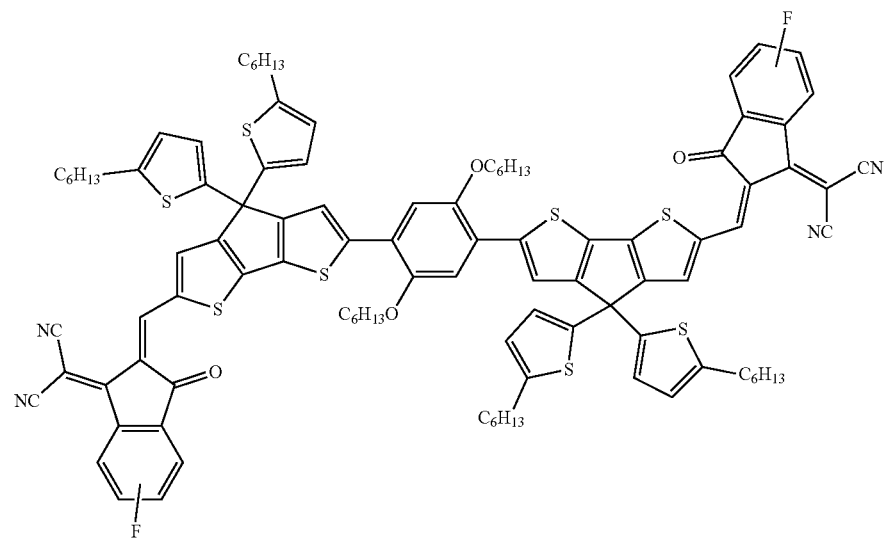

[Compound 7]

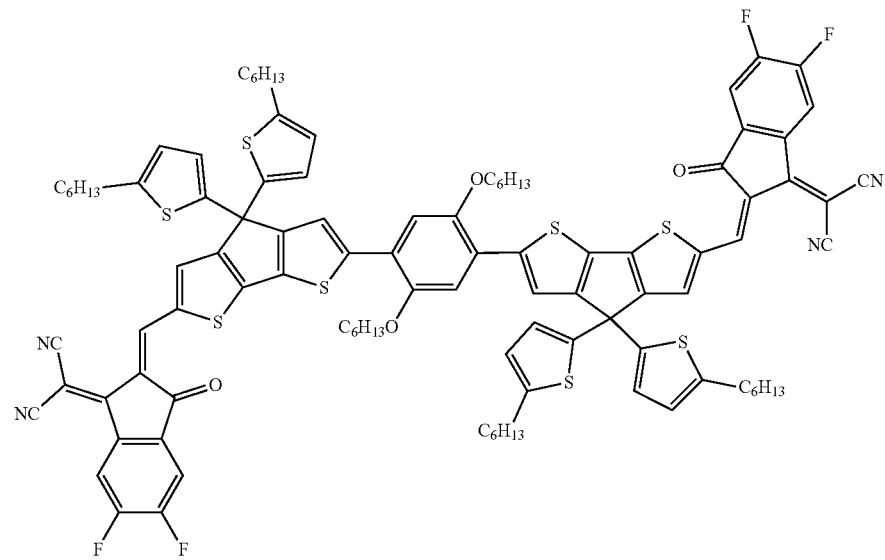

[Compound 8]

[Compound 9]
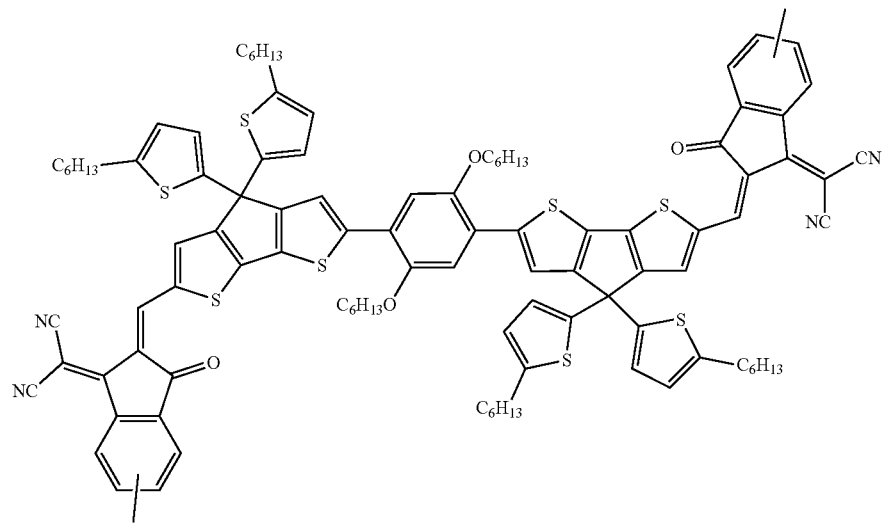
[Compound 10]
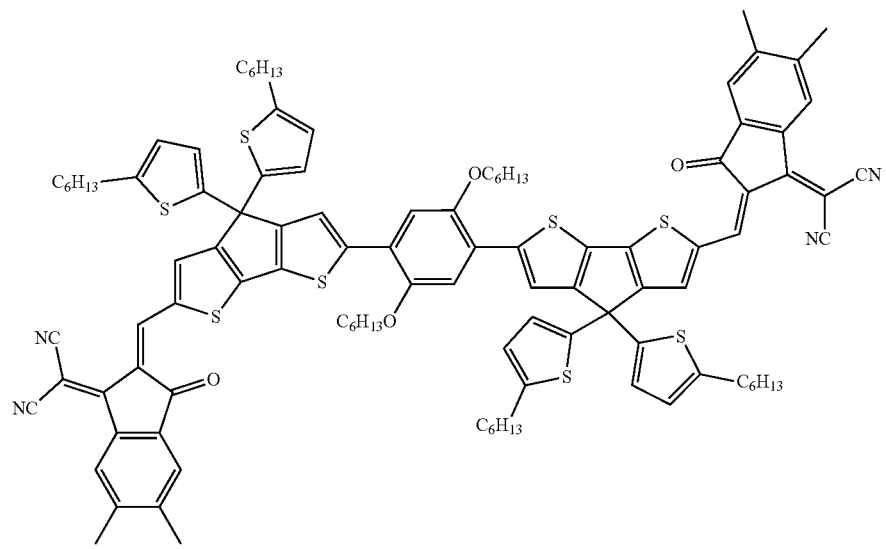
Preparation Example 5. Preparation of Compound 11
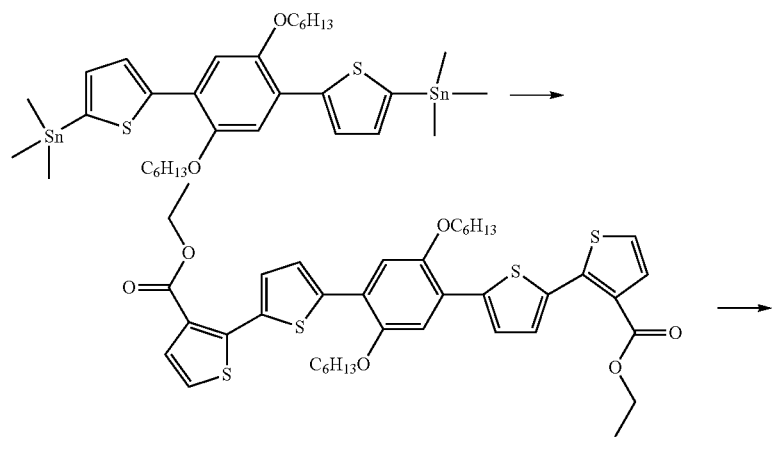
Compound A

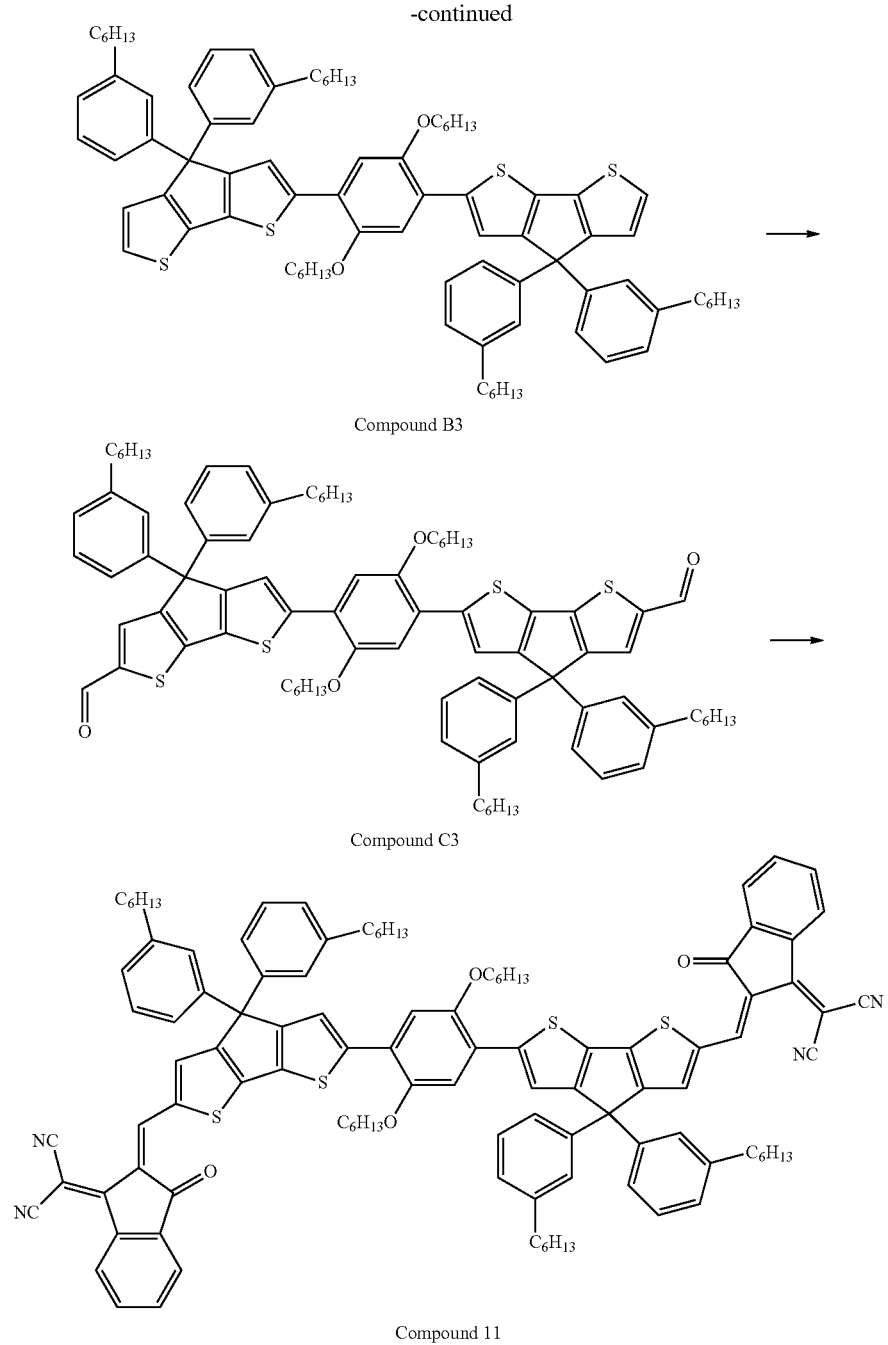

Compound B3

Compound C3

Compound 11

(1) Preparation of Compound B3

Compound B3 was prepared by performing the same process as in (2) of Preparation Example 1, except that 1-bromo-3-hexylbenzene was used instead of 1-bromo-4-hexylbenzene in (2) of Preparation Example 1.

(2) Preparation of Compound C3

Compound C3 was prepared by performing the same process as in (3) of Preparation Example 1, except that Compound B3 was used instead of Compound B in (3) of Preparation Example 1.

(3) Preparation of Compound 11

Compound 11 was prepared by performing the same process as in (4) of Preparation Example 1, except that Compound C3 was used instead of Compound C in (4) of Preparation Example 1.

Preparation Example 6. Preparation of Formulae 12 to 15

The following Compounds 12 to 15 were prepared by performing the same process as in Preparation Example 5, except that the respective materials in the following Table 3 were used instead of 2-(3-oxo-2,3-dihydro-1H-inden-1-ylidene)malononitrile in (3) of Preparation Example 5.

TABLE 3

| Target compound | Used material |
| --- | --- |
| Compound 12 | Compound in which 2-(6-fluoro-3-oxo-2,3-dihydro-1H-inden-1-ylidene)malononitrile and 2-(5-fluoro-3-oxo-2,3-dihydro-1H-inden-1-ylidene)malononitrile are mixed at a mass ratio of 3:7 |
| Compound 13 | (2-(5,6-difluoro-3-oxo-2,3-dihydro-1H-inden-1-ylidene)malononitrile) |
| Compound 14 | Compound in which 2-(6-methyl-3-oxo-2,3-dihydro-1H-inden-1-ylidene)malononitrile and 2-(5-methyl-3-oxo-2,3-dihydro-1H-inden-1-ylidene)malononitrile are mixed at a mass ratio of 3:7 |
| Compound 15 | 2-(5,6-dimethyl-3-oxo-2,3-dihydro-1H-inden-1-ylidene)malononitrile |

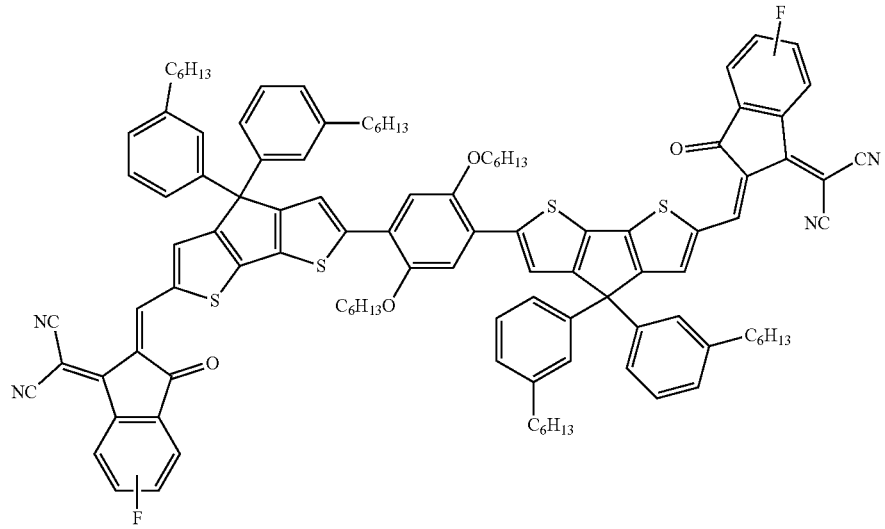

[Compound 12]

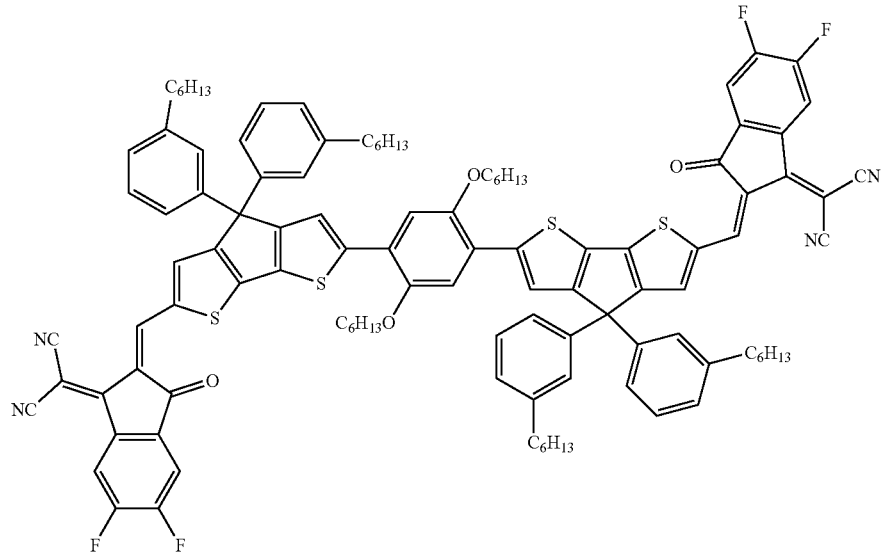

[Compound 13]

[Compound 14]

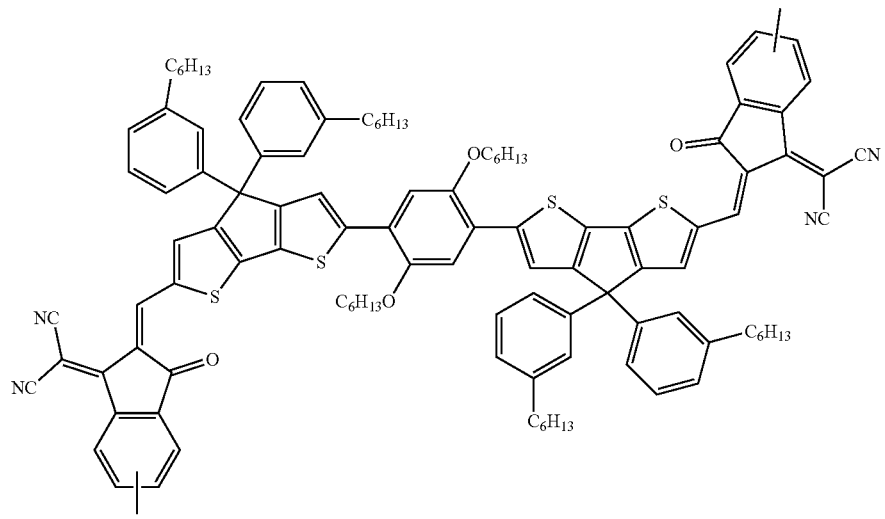

[Compound 15]

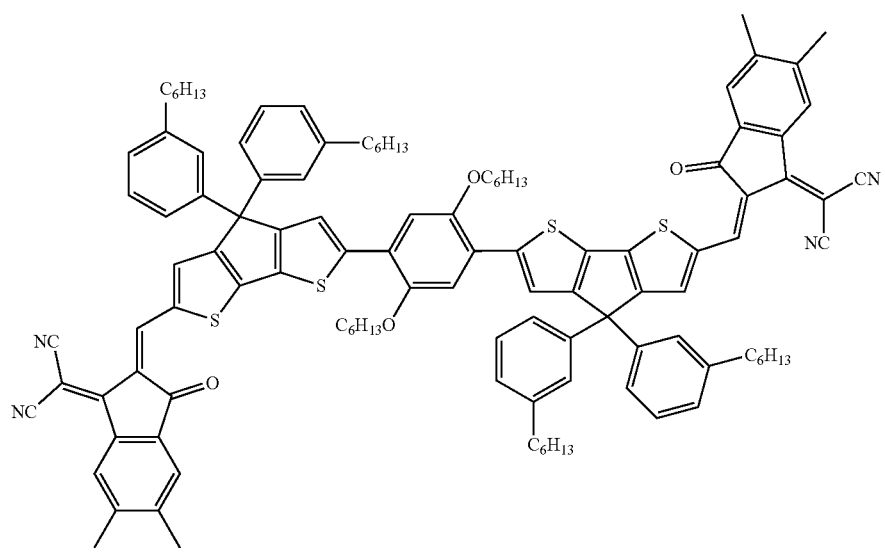

EXAMPLES: MANUFACTURE OF ORGANIC SOLAR CELL

Example 1

(1) Preparation of Composite Solution

A composite solution at a concentration of 2 wt % was prepared by dissolving the following compound poly[(2,6-(4,8-bis(5-(2-ethylhexyl)thiophen-2-yl)-benzo[1,2-b:4,5-b']dithiophene))-alt-(5,5-(1',3'-di-2-thienyl-5',7'-bis(2-ethylhexyl)benzo[1',2'-c:4',5'-c']dithiophene-4,8-dione))] (PBDB-T) (Mn: 25,000 g/mol, manufactured by Solarmer Materials Inc.) as an electron donor material and Compound 1 synthesized in the Preparation Example as an electron acceptor material at a mass ratio of 1:1 in chlorobenzene (CB).

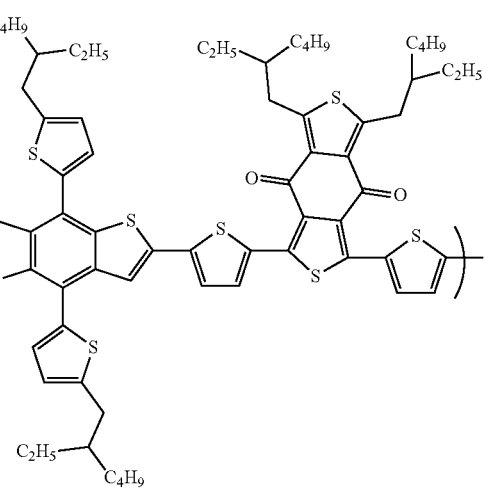

PBDB-T

(2) Manufacture of Organic Solar Cell

A glass substrate (11.5Ω/□) coated with bar-type ITO in 1.5×1.5 cm$^2$ was ultrasonically washed by using distilled water, acetone, and 2-propanol, and the ITO surface was treated with ozone for 10 minutes to form a first electrode.

After the first electrode was spin-coated with a ZnO nanoparticle solution (N-10, Nanograde Ltd, 2.5 wt % in 1-butanol, filtered with 0.45 μm PTFE) for 40 seconds, the remaining solvent was removed by a heat treatment at 80° C. for 10 minutes to form an electron transport layer.

Thereafter, the electron transport layer was spin-coated with the composite solution prepared in (1) at 70° C. and 1,300 rpm for 25 seconds to form a photoactive layer, and MoO$_3$ was thermally deposited to have a thickness of 10 nm onto the photoactive layer at a rate of 0.2 Å/s under a vacuum of 10$^{-7}$ torr to form a hole transport layer.

Thereafter, an organic solar cell having an inverted structure was manufactured by depositing Ag to have a thickness of 100 nm at a rate of 1 Å/s in a thermal depositor to form a second electrode.

Example 2

An organic solar cell was manufactured by performing the same process as in Example 1, except that the composite solution prepared in (1) was spin-coated at 1,400 rpm during the formation of the photoactive layer in Example 1.

Example 3

An organic solar cell was manufactured by performing the same process as in Example 1, except that the composite solution prepared in (1) was spin-coated at 1,500 rpm during the formation of the photoactive layer in Example 1.

Example 4

An organic solar cell was manufactured by performing the same process as in Example 1, except that the composite solution prepared in (1) was spin-coated at 1,600 rpm during the formation of the photoactive layer in Example 1.

Comparative Example 1

An organic solar cell was manufactured by performing the same process as in Example 1, except that the following comparative compound was used instead of Compound 1 during the preparation of the composite solution in Example 1.

[Comparative Compound]

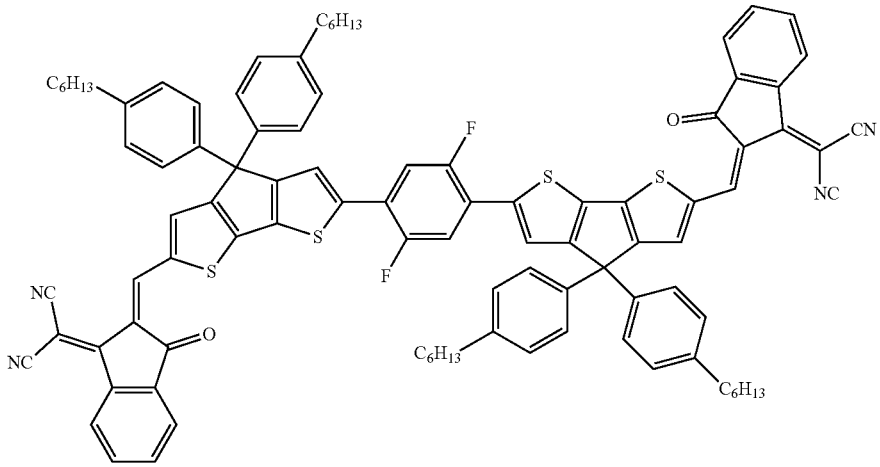

Comparative Example 2

An organic solar cell was manufactured by performing the same process as in Comparative Example 1, except that the composite solution was spin-coated at 1,400 rpm during the formation of the photoactive layer in Comparative Example 1.

Comparative Example 3

An organic solar cell was manufactured by performing the same process as in Comparative Example 1, except that the composite solution was spin-coated at 1,500 rpm during the formation of the photoactive layer in Comparative Example 1.

Comparative Example 4

An organic solar cell was manufactured by performing the same process as in Comparative Example 1, except that the composite solution was spin-coated at 1,600 rpm during the formation of the photoactive layer in Comparative Example 1.

The photoelectric conversion characteristics of the organic solar cells manufactured in Examples 1 to 4 and Comparative Examples 1 to 4 were measured under the condition of 100 mW/cm$^2$ (AM 1.5), and the results are shown in the following Table 4.

TABLE 4

| Composite Solution | | Spin-speed (rpm) | Voc (V) | Jsc (mA/cm2) | FF | η (%) | Average η (%) |
|---|---|---|---|---|---|---|---|
| PBDB-T + Compound 1 | Example 1 | 1,300 | 0.909 | 15.467 | 0.652 | 9.17 | 9.19 |
| | | | 0.907 | 15.833 | 0.641 | 9.21 | |
| | Example 2 | 1,400 | 0.896 | 15.400 | 0.648 | 8.94 | 8.91 |
| | | | 0.893 | 15.703 | 0.633 | 8.88 | |
| | Example 3 | 1,500 | 0.913 | 15.195 | 0.655 | 9.09 | 8.68 |
| | | | 0.888 | 15.298 | 0.609 | 8.27 | |
| | Example 4 | 1,600 | 0.902 | 15.232 | 0.654 | 8.98 | 9.14 |
| | | | 0.899 | 16.018 | 0.646 | 9.30 | |
| PBDB-T + Comparative Compound | Comparative Example 1 | 1,300 | 0.894 | 14.521 | 0.586 | 7.61 | 6.98 |
| | | | 0.835 | 14.653 | 0.519 | 6.35 | |
| | Comparative Example 2 | 1,400 | 0.908 | 15.006 | 0.611 | 8.33 | 8.55 |
| | | | 0.910 | 15.420 | 0.625 | 8.77 | |
| | Comparative Example 3 | 1,500 | 0.899 | 14.907 | 0.612 | 8.20 | 8.20 |
| | | | 0.896 | 14.903 | 0.613 | 8.19 | |
| | Comparative Example 4 | 1,600 | 0.876 | 14.728 | 0.599 | 7.73 | 7.78 |
| | | | 0.875 | 14.790 | 0.604 | 7.82 | |

In Table 4, the spin-speed, $V_{OC}$, $J_{SC}$, FF, and η mean a rotation speed of an apparatus when the photoactive layer is formed by spin-coating the electron transport layer with the composite solution, an open-circuit voltage, a short-circuit current, a fill factor, and energy conversion efficiency, respectively. The open-circuit voltage and the short-circuit current are an X axis intercept and a Y axis intercept, respectively, in the fourth quadrant of the voltage-current density curve, and as the two values are increased, the efficiency of the solar cell is preferably increased. In addition, the fill factor is a value obtained by dividing the area of a rectangle, which may be drawn within the curve, by the product of the short-circuit current and the open-circuit voltage. The energy conversion efficiency (η) may be obtained by dividing the product of the open-circuit voltage ($V_{oc}$), the short-circuit current ($J_{sc}$), and the fill factor (FF) by the intensity ($P_{in}$) of incident light, and the higher the value is, the more preferred energy conversion efficiency (η) is.

$$\eta = \frac{V_{oc} J_{sc} FF}{P_{in}}$$

From the results in Table 4, it can be seen that the organic solar cells in Examples 1 to 4 where Compound 1 according to an exemplary embodiment of the present specification is used as an electron acceptor have a high open-circuit voltage, excellent device efficiency such as a fill factor, and excellent energy conversion efficiency, as compared to the organic solar cells in Comparative Examples 1 to 4 where the comparative compound in which F is substituted at the —OR11 position of Formula 1 of the present application is used.

Specifically, the organic solar cell including Compound 1 may have a high FF value, and consequently, the organic solar cell including Compound 1 may exhibit high energy conversion efficiency of 8.6% or more, preferably 9% or more.

Figure 3:
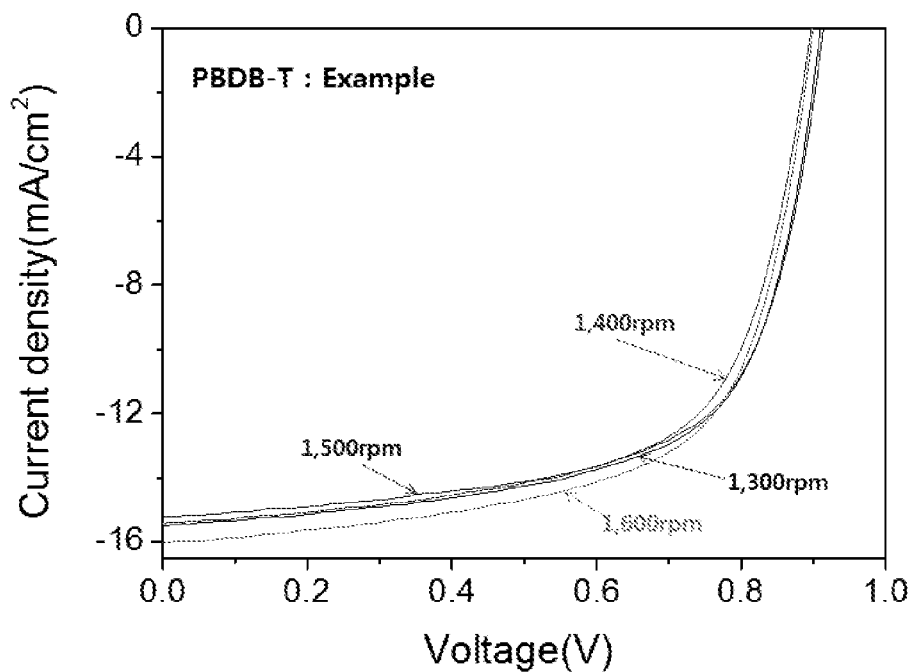
FIG. 3 is a view illustrating the current density according to the voltage with regard to organic solar cells manufactured in Examples 1 to 4 of the present specification.
Figure 4:
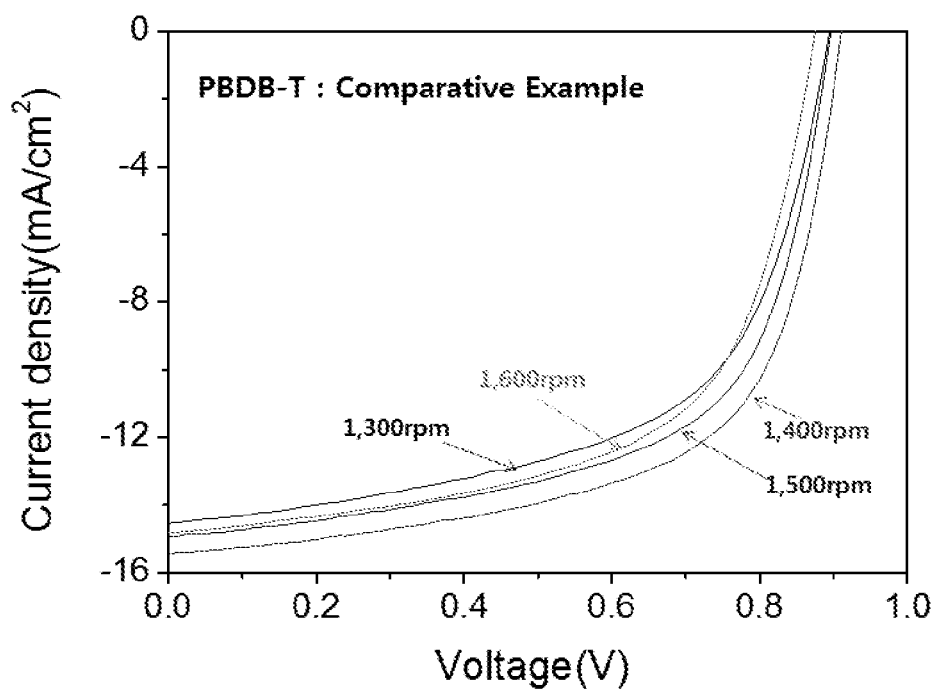
FIG. 4 is a view illustrating the current density according to the voltage with regard to organic solar cells manufactured in Comparative Examples 1 to 4 of the present specification.

Furthermore, FIGS. 3 and 4 are views illustrating photoelectric conversion characteristics of the organic solar cells manufactured in the Examples and the Comparative Examples, and from FIGS. 3 and 4, it can be confirmed that the organic solar cells manufactured in the Examples have smaller deviations of the performance according to the manufacturing conditions than those of the organic solar cells in the Comparative Examples.

What is claimed is:
1. A heterocyclic compound represented by the following of Formula 1:

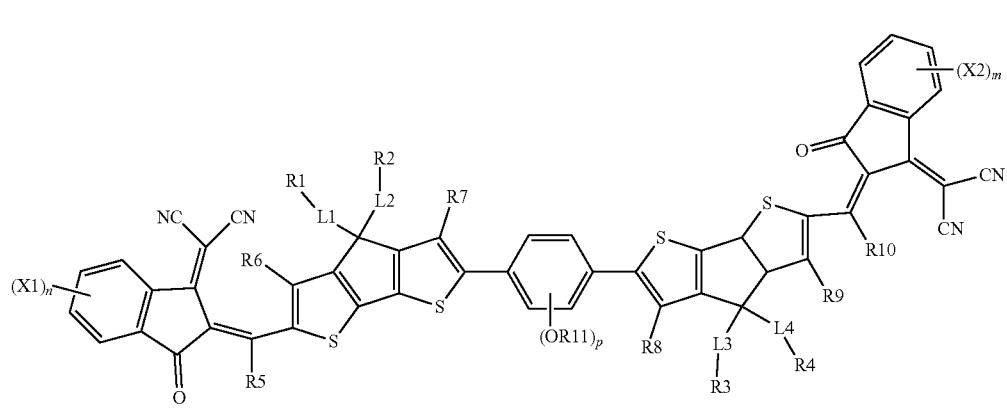

[Formula 1]

wherein:

L1 to L4 are each independently a substituted or unsubstituted arylene group or a substituted or unsubstituted divalent heterocyclic group;

R1 to R11 are each independently hydrogen or a substituted or unsubstituted alkyl group;

X1 and X2 are each independently hydrogen a substituted or unsubstituted alkyl group, or a halogen group; and m, n, and p are each independently an integer of from 1 to 4.

2. An organic electronic device comprising:

a first electrode;

a second electrode on the first electrode; and an organic material layer comprising one or more layers, wherein the organic material layer is between the first electrode and the second electrode and comprises an organic active layer, and wherein the organic active layer comprises the heterocyclic compound of claim 1.

3. The organic electronic device of claim 2, wherein the organic active layer comprises an electron donor and an electron acceptor, and the electron acceptor comprises the heterocyclic compound.

4. The organic electronic device of claim 2, wherein the organic electronic device is an organic solar cell, an organic photoelectric device, an organic light emitting device, an organic photoconductor, or an organic transistor.

5. A method for manufacturing an organic electronic device, the method comprising:

forming a first electrode on a substrate;

forming an electron transport layer on the first electrode;

forming an organic material layer comprising one or more layers and comprising an organic active layer on the electron transport layer; and forming a second electrode on the organic material layer, wherein the organic active layer comprises the heterocyclic compound of claim 1.

6. The method of claim 5, wherein the forming the organic material layer comprises performing a spin-coating process with a spinning rate in a range of from 1,300 rpm to 1,600 rpm.

7. The heterocyclic compound of claim 1, wherein the heterocyclic compound of Formula 1 is a compound of Formula 1-1:

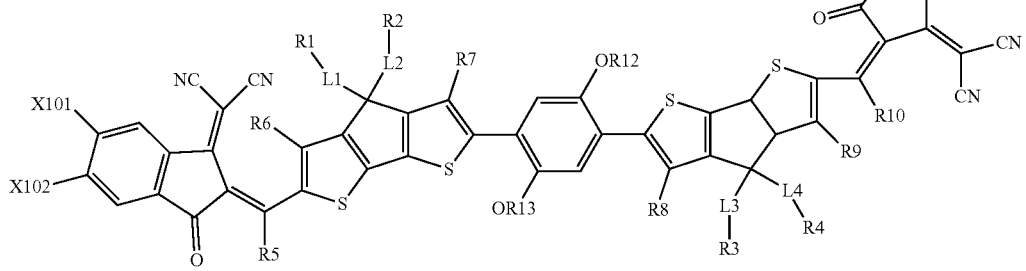

[Formula 1-1]

wherein:

R1 to R10 and L1 to L4 are the same as those defined in Formula 1;

R12 and R13 are each independently hydrogen or a substituted or unsubstituted alkyl group; and X101, X102, X201, and X202 are each independently hydrogen, a substituted or unsubstituted alkyl group, or a halogen group.

8. The heterocyclic compound of claim 1, wherein X1 and X2 are each fluorine.

9. The heterocyclic compound of claim 1, wherein the heterocyclic compound of Formula 1 is a compound of Formula 1-2:

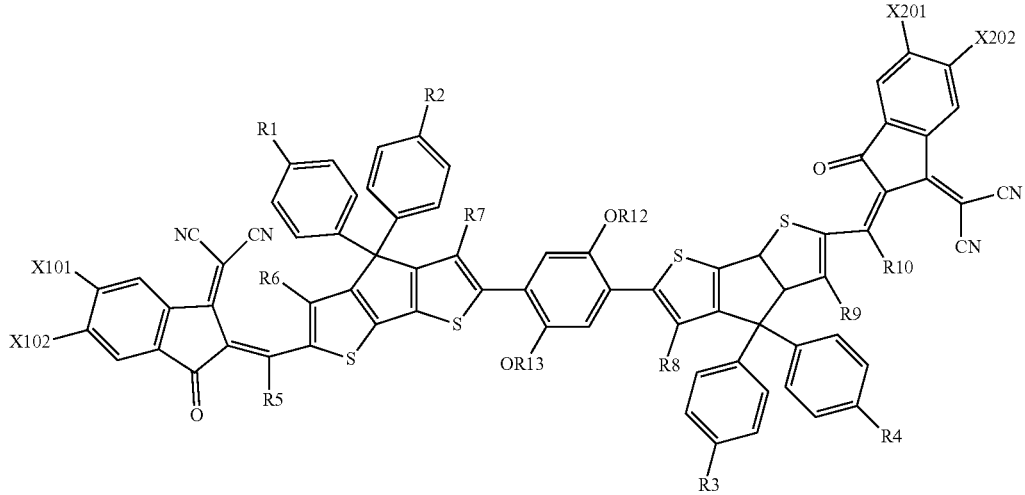

[Formula 1-2]

wherein:
R1 to R10 are the same as those defined in Formula 1;
R12 and R13 are each independently hydrogen or a substituted or unsubstituted alkyl group; and
X101, X102, X201, and X202 are each independently hydrogen, a substituted or unsubstituted alkyl group, or a halogen group.

10. The heterocyclic compound of claim 1, wherein R1 to R4 are each independently a straight-chained or branched alkyl group having from 1 to 10 carbon atoms.

11. The heterocyclic compound of claim 1, wherein R11 is a straight-chained or branched alkyl group having from 1 to 10 carbon atoms.

12. The heterocyclic compound of claim 1, wherein the heterocyclic compound of Formula 1 is a compound of any one of Formulae 2-1 to 2-15:

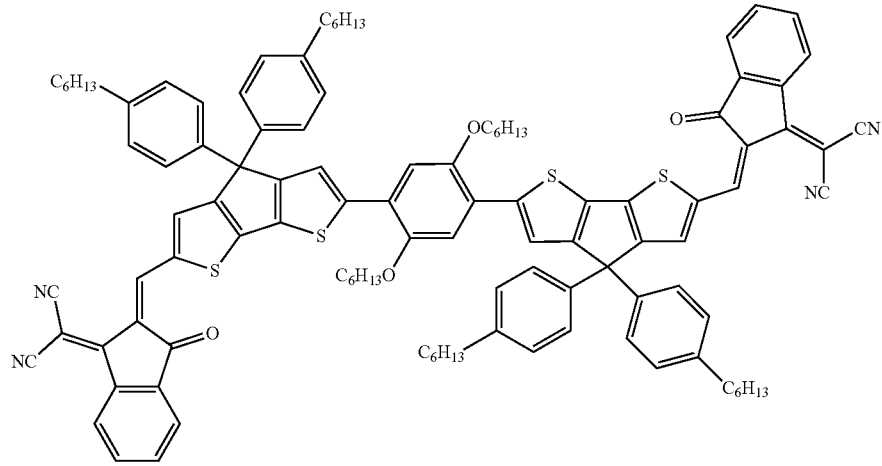

[Formula 2-1]

-continued
[Formula 2-2]
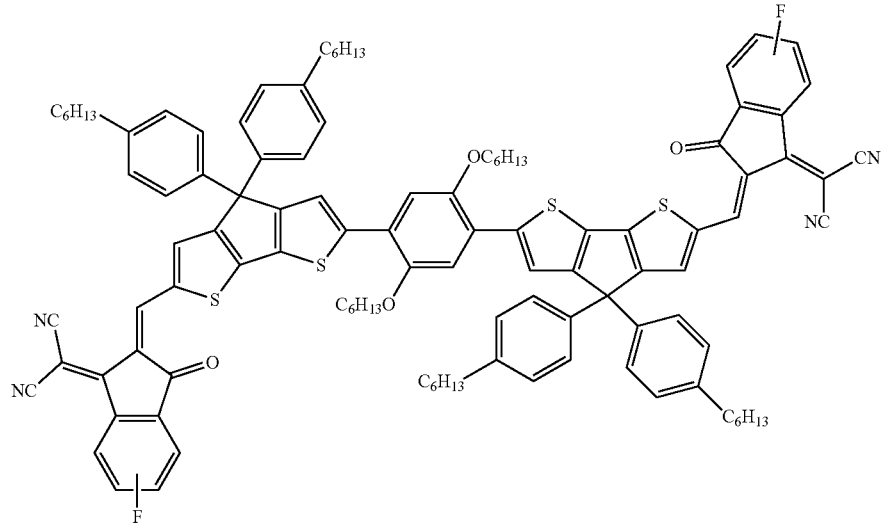
[Formula 2-3]
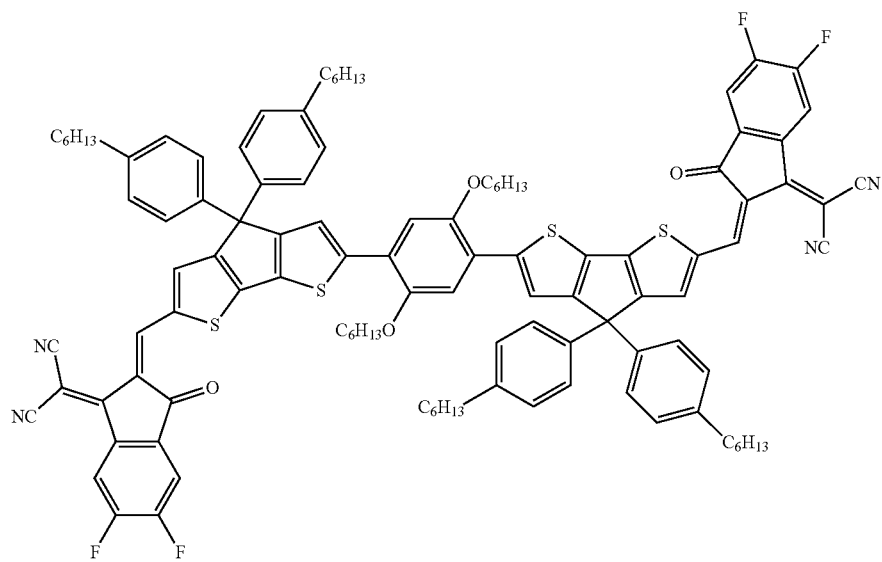
[Formula 2-4]
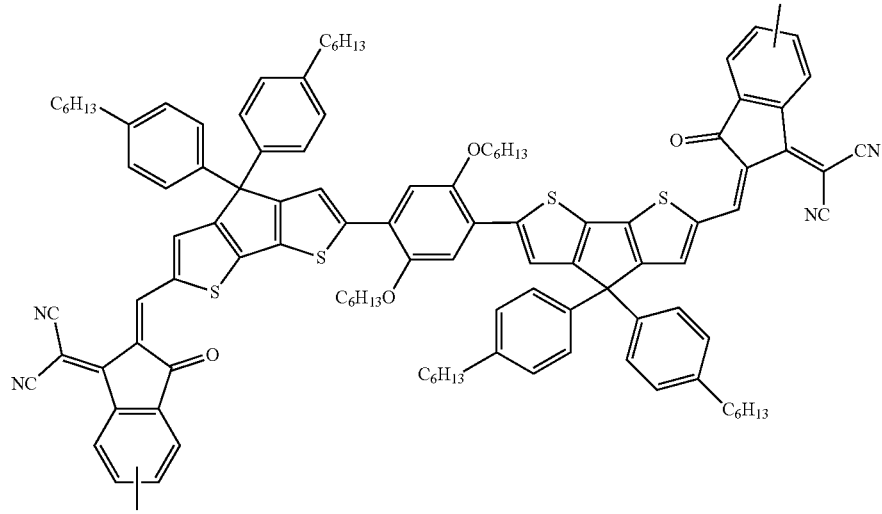

[Formula 2-5]
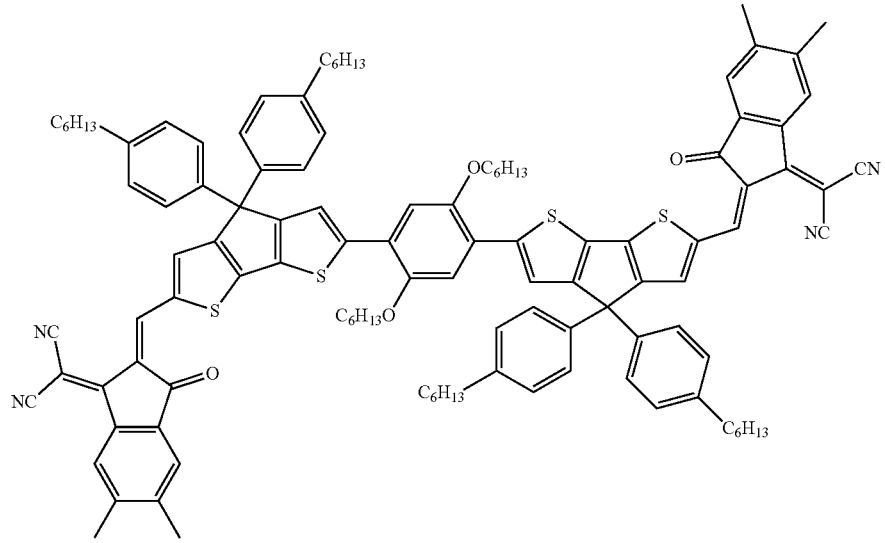
[Formula 2-6]
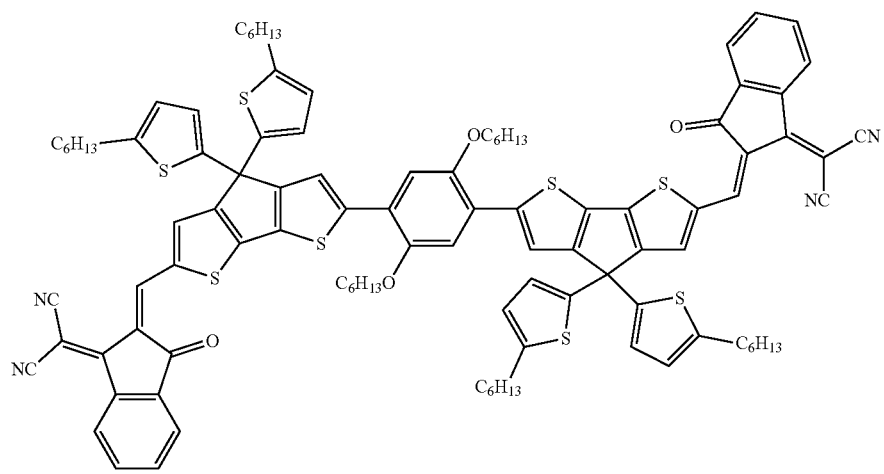
[Formula 2-7]
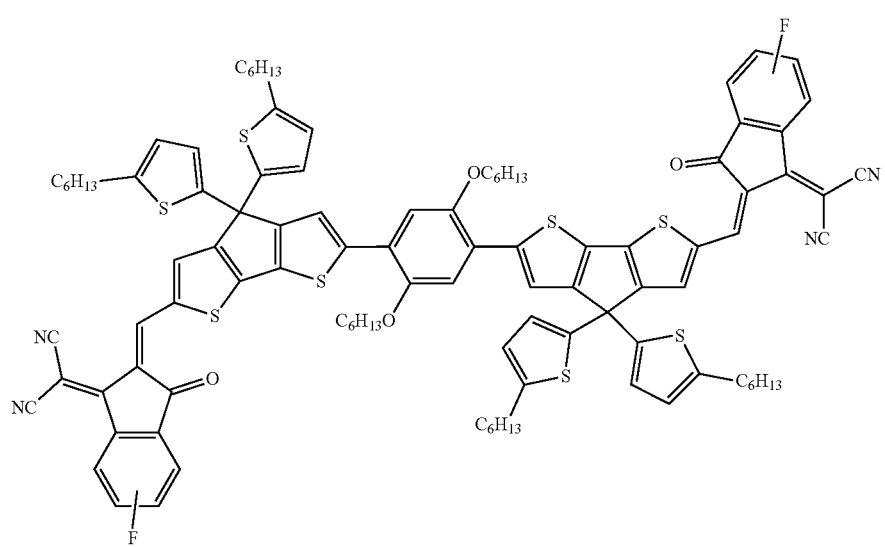

[Formula 2-8]
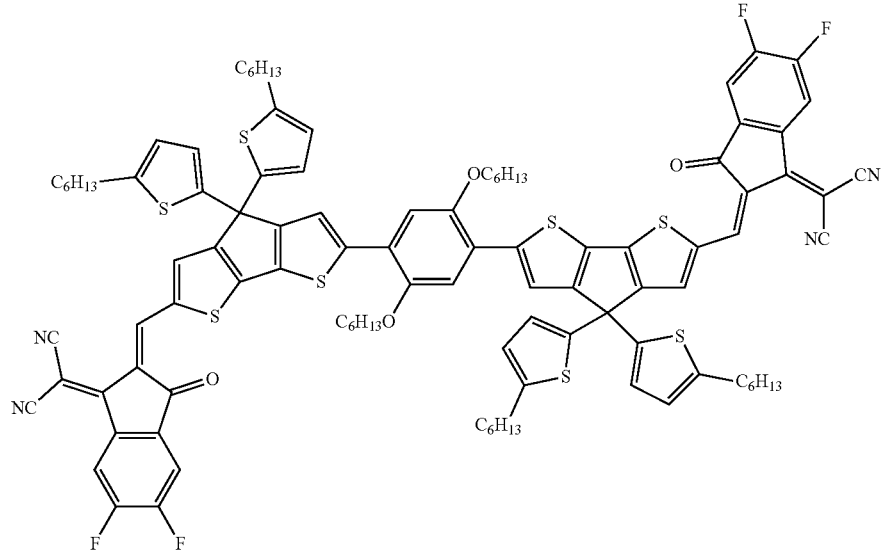
[Formula 2-9]
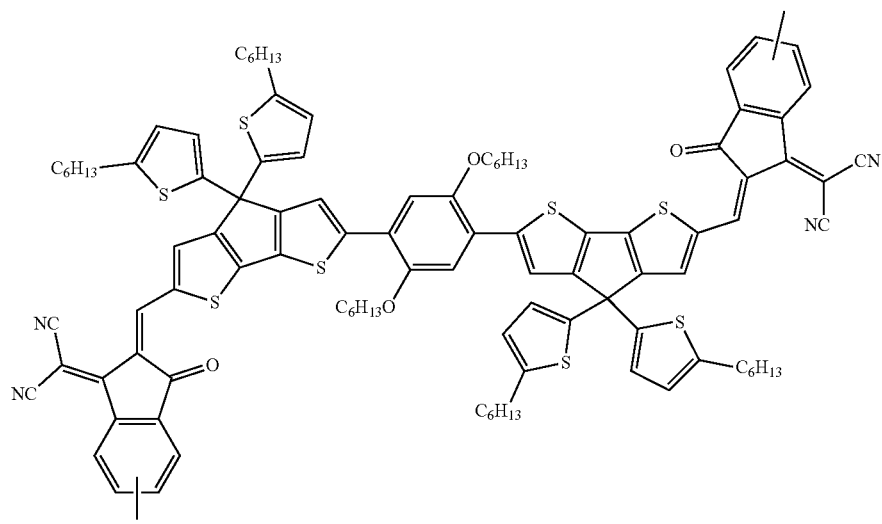
[Formula 2-10]
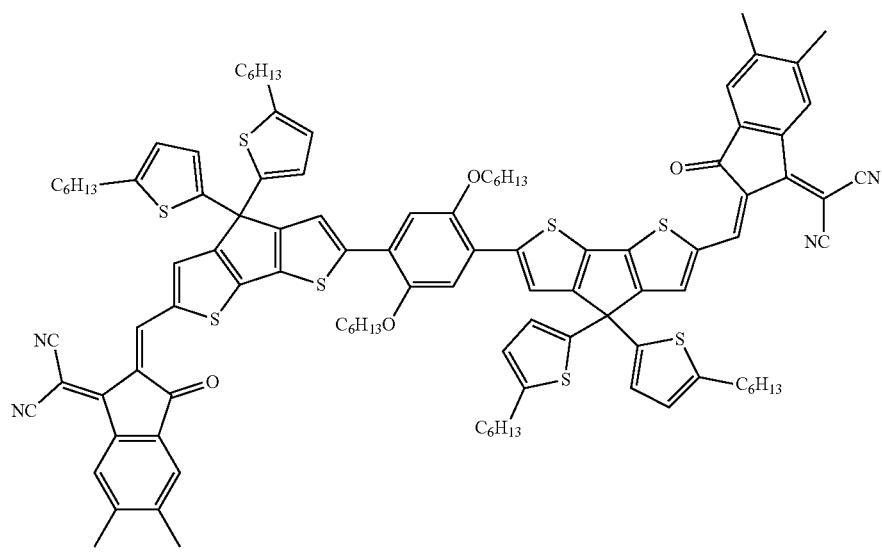

[Formula 2-11]
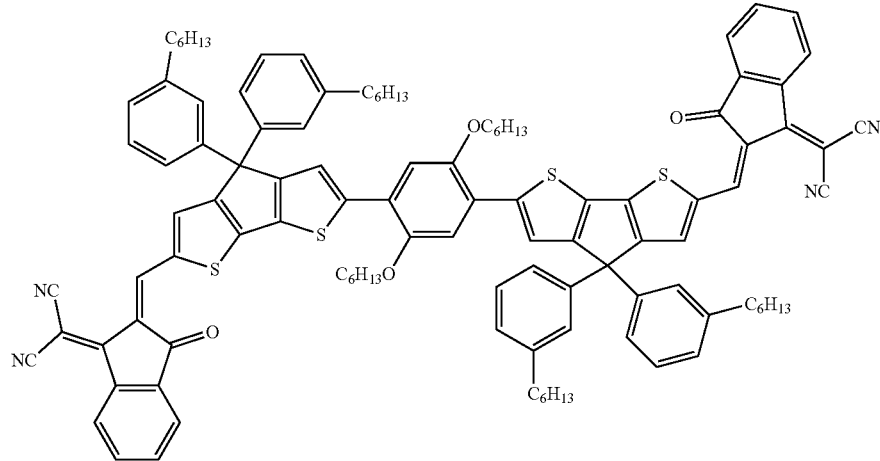
[Formula 2-12]
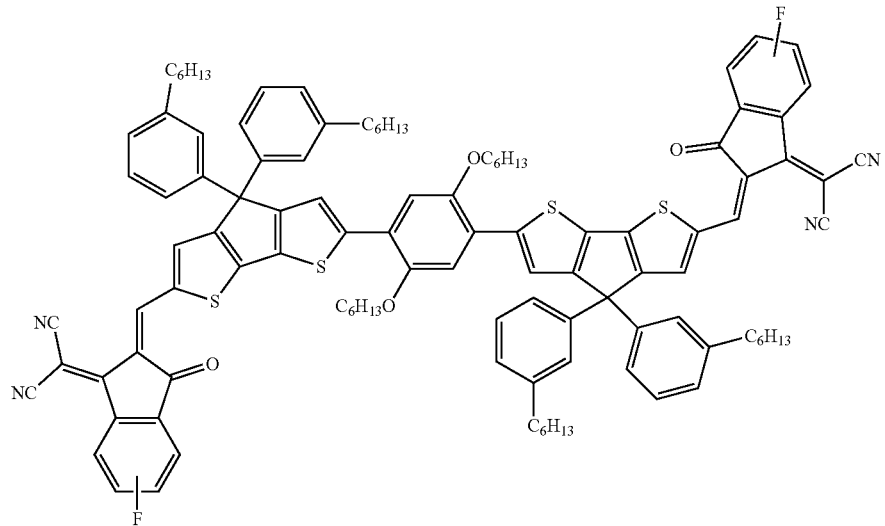
[Formula 2-13]
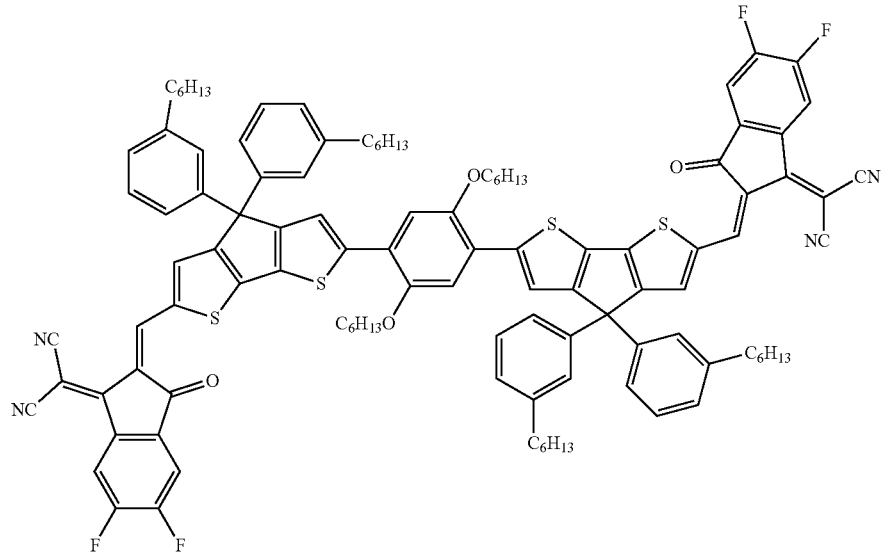

[Formula 2-14]
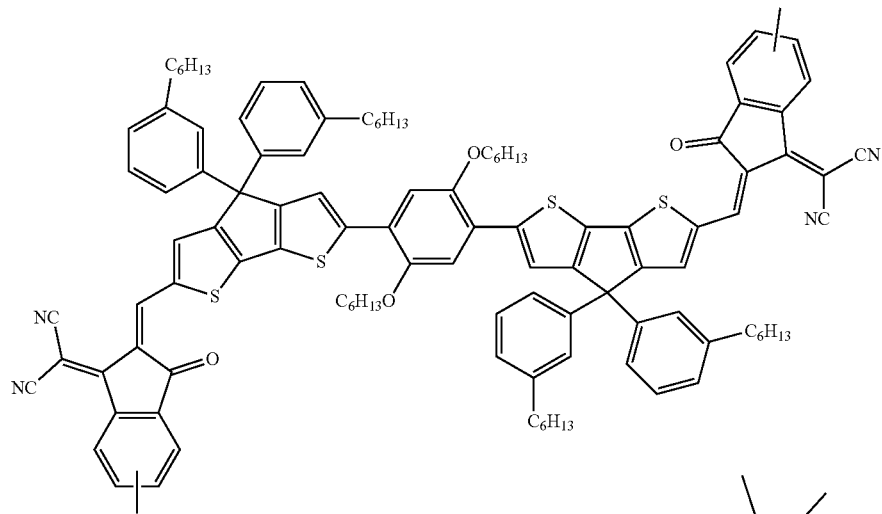
[Formula 2-15]
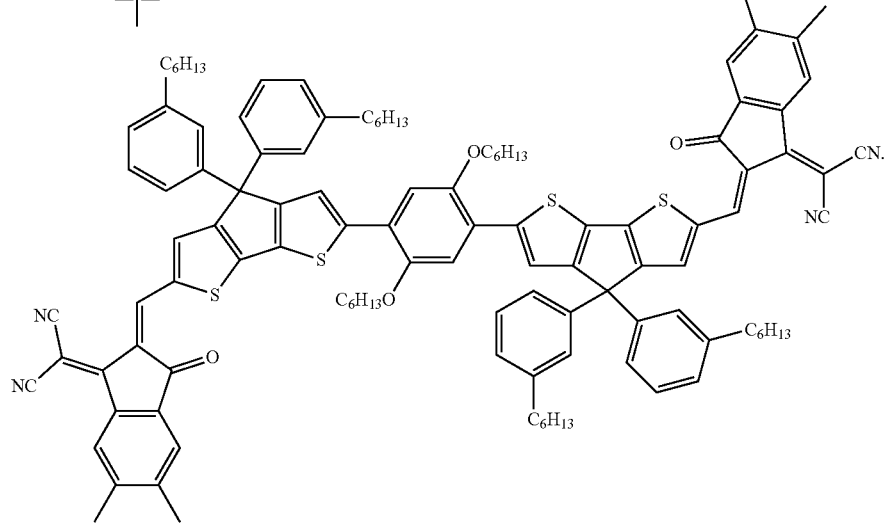
13. The heterocyclic compound of claim 1, wherein the heterocyclic compound of Formula 1 is a compound of Formula 1-3:
[Formula 1-3]
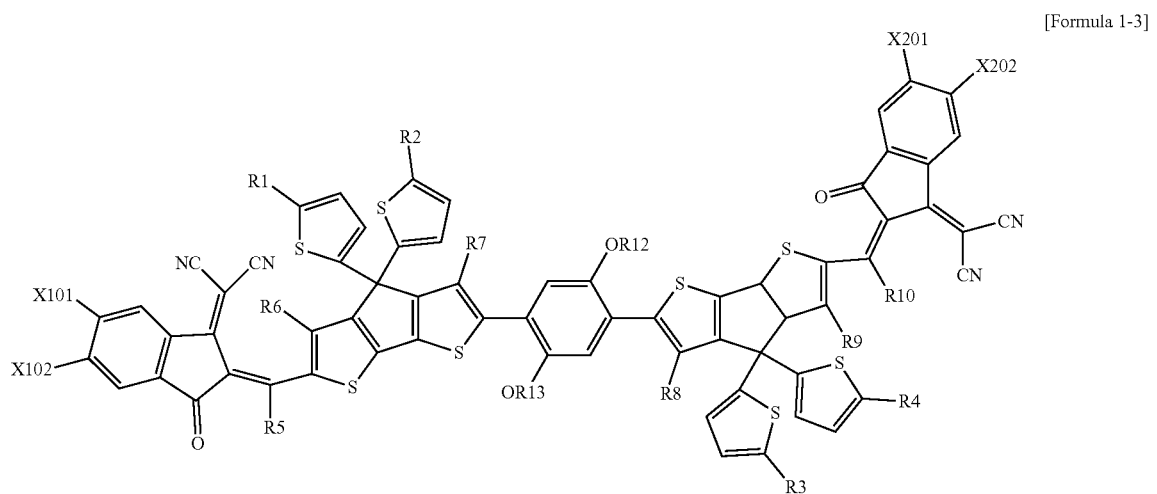

wherein:

R1 to R10 are the same as those defined in Formula 1;

R12 and R13 are each independently hydrogen or a substituted or unsubstituted alkyl group; and X101, X102, X201, and X202 are each independently hydrogen, a substituted or unsubstituted alkyl group, or a halogen group.

* * * * *